(12) United States Patent
Priestley et al.

(10) Patent No.: US 6,803,374 B2
(45) Date of Patent: Oct. 12, 2004

(54) COMPOUNDS USEFUL FOR TREATING HEPATITIS C VIRUS

(75) Inventors: Eldon Scott Priestley, Hockessin, DE (US); Carl P. Decicco, Kennett Square, PA (US); Thomas W. Hudyma, Durham, CT (US); Xiaofan Zheng, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/648,873

(22) Filed: Aug. 27, 2003

(65) Prior Publication Data

US 2004/0067976 A1 Apr. 8, 2004

Related U.S. Application Data

(63) Continuation of application No. 10/259,041, filed on Sep. 26, 2002, now abandoned.
(60) Provisional application No. 60/324,874, filed on Sep. 26, 2001.

(51) Int. Cl.[7] ..................... A61K 31/44; A61K 31/415; C07D 235/04; C07D 515/02
(52) U.S. Cl. .................... 514/303; 514/394; 548/304.7; 548/305.1; 546/113
(58) Field of Search ....................... 546/113; 548/304.7, 548/305.1; 514/303, 394

(56) References Cited

FOREIGN PATENT DOCUMENTS

| | | |
|---|---|---|
| EP | 1 162 196 A1 | 12/2000 |
| WO | WO 00/06529 | 2/2000 |
| WO | WO 00/10573 | 3/2000 |
| WO | WO 00/13708 | 3/2000 |
| WO | WO 00/18231 | 4/2000 |
| WO | WO 01/032153 A2 | 5/2001 |
| WO | WO 01/85172 A1 | 11/2001 |
| WO | WO 02/06246 A1 | 1/2002 |

OTHER PUBLICATIONS

US 2003050320 "Preparation of substitutd 1–cyclohexyl–2–phenylbenzimidazole–5–carboxylic acids as remedies for hepatitis C", Hashimoto et. al.*
Lauer et al. (2001) New England Journal of Medicine, vol. 345, No. 1, pp. 41–52.
Poynard et al. (1998) The Lancet, vol. 352, pp. 1426–1432.
Kolykhalov et al. (2000) Journal of Virology, vol. 74, No. 4, pp. 2046–2051.
Hashimoto et al. (2001) Chemical Abstracts, vol. 135, No. 6, p. 783, Abstract No. 76874q.

* cited by examiner

*Primary Examiner*—Johann Richter
*Assistant Examiner*—Binta Robinson
(74) *Attorney, Agent, or Firm*—Warren K. Volles

(57) ABSTRACT

A series of compounds of Formula I are disclosed which are useful in treating viral hepatitus C.

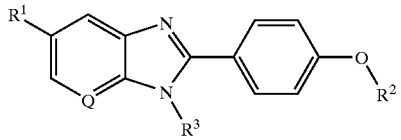

15 Claims, No Drawings

COMPOUNDS USEFUL FOR TREATING HEPATITIS C VIRUS

CROSS-REFERENCE TO RELATED APPLICATIONS

This application is a continuation of U.S. patent application Ser. No. 10/259,041, filed Sep. 26, 2002 now abandoned and claims the benefit of U.S. provisional application Ser. No. 60/324,874 filed Sep. 26, 2001.

FIELD OF THE INVENTION

The present invention is directed to compounds which inhibit the RNA-dependent RNA polymerase (RdRp) encoded by Hepatitis C virus (HCV). The compounds, or pharmaceutically acceptable salts or prodrugs thereof, are of value in the treatment and/or prevention of infection by HCV.

BACKGROUND OF THE INVENTION

The Field of the Invention. HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. (Lauer, G. M.; Walker, B. D. *N. Engl. J. Med.* (2001), 345, 41–52).

Presently, the most effective HCV therapy employs a combination of alpha-interferon and ribavirin, leading to sustained efficacy in 40% of patients. (Poynard, T. et al. *Lancet* (1998), 352, 1426–1432). Recent clinical results demonstrate that pegylated alpha-interferon is superior to unmodified alpha-interferon as monotherapy (Zeuzem, S. et al. *N. Engl. J. Med.* (2000), 343, 1666–1672). However, even with experimental therapeutic regimens involving combinations of pegylated alpha-interferon and ribavirin, a substantial fraction of patients do not have a sustained reduction in viral load. In addition, the prospects for development of a prophylactic or therapeutic vaccine appear dim, in spite of intensive research efforts. Thus, there is a clear and long-felt need to develop effective therapeutics for treatment of HCV infection.

HCV is a positive-stranded RNA virus. Based on comparison of deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The RNA genome is about 9.6 Kb in length, and encodes a single polypeptide of about 3000 amino acids. The 5' untranslated region contains an internal ribosome entry site (IRES), which directs cellular ribosomes to the correct AUG for initiation of translation. The translated product contains the following proteins: core-E1-E2-p7-NS2-NS3-NS4A-NS4B-NS5A-NS5B. This precursor protein is cotranslationally and posttranslationally processed into at least 10 viral structural (core, E1, E2) and nonstructural (NS2-NS5B) proteins by the action of host cell signal peptidase and by two distinct viral proteinase activities (NS2/3 and NS3).

Although the functions of the NS proteins are not completely defined, it is known that NS3 is a serine protease/RNA helicase, NS4A is a protease cofactor, and NS5B is an RNA dependent RNA polymerase involved in viral replication. It has recently been demonstrated that functional NS5B is required for virus infectivity in chimpanzees (Kolykhalov, A. A. et al. *J. Virol.* (2000), 74, 2046–2051). This result strongly suggests that inhibition of the NS5B RdRp is a viable approach for the development of HCV therapeutic agents.

Description of Related Art. Efforts toward the development of HCV NS5B RdRp inhibitors have resulted in the following disclosures:

Altamura et al. (Istituto Di Ricerche Di Biologia Molecolare) describe diketoacid RdRp inhibitors (WO 00/06529 and WO 02/06246 A1). Altamura et al. suggest that the diketoacids and dihydroxypyriridine carboxylic acids inhibit HCV RdRp by interfering with the binding of phosphoryl groups at the active site of the enzyme.

A series of three disclosures from Viropharma Inc. (Bailey, T. R. et al, WO 00/10573; Bailey, T. R. et al, WO 00/13708; Young, D. C. et al, WO 00/18231) describe HCV RdRp inhibitors. WO 00/10573 covers a series of rhodanine derivatives, WO 00/13708 covers a series of barbituric acid or thiobarbituric acid derivatives, and WO 0018231 covers a series of dihydrobenzothiophene derivatives.

R. Storer (Biochem Pharma, Inc.) has disclosed the use of a series of dioxolane nucleosides for treatment of HCV (WO 01/32153).

EP 1162196 (Japan Tobacco Inc.) discloses a series of fused ring heterocycles as inhibitors of HCV RdRp. These compounds may be distinguished from the applicants' compounds in the nature of the "A" substituent in applicants' Formula I compounds.

WO 02/04425 (Boehringer Ingelheim) discloses a series of HCV NS5B polymerase inhibitors which also may be distinguished from the applicants' compounds in the nature of the "A" substituent in applicants' Formula I compounds.

WO 01/85172 (Smithkline Beecham) discloses a series of 1-(alkyl)-3-(1,1-dioxo-2H-benzo-1,2,4-thiadiazin-3-yl)-4-hydroxy-2-quinolones as HCV inhibitors.

SUMMARY OF THE INVENTION

The present invention is directed to compounds according to Formula I:

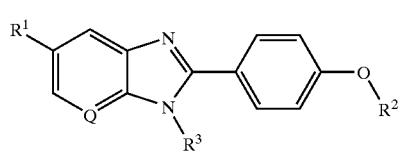

wherein all represented groups are defined below.

The present invention is also directed to compounds of Formula I, or pharmaceutically acceptable salts or prodrugs thereof, which are useful as inhibitors of HCV NS5B RdRp. It is another object of the present invention to provide pharmaceutical compositions comprising a pharmaceutically acceptable carrier and a therapeutically effective amount of a compound of Formula I, or pharmaceutically acceptable salt or prodrug thereof. It is another object of the present invention to provide a method for the treatment or prevention of HCV comprising administering to a host in need of such treatment a therapeutically effective amount of a compound of Formula I, or a pharmaceutically acceptable salt or prodrug thereof. These and other objects of the invention, which will become apparent during the following detailed description, have been achieved by the discovery that compounds of Formula I inhibit the HCV NS5B RdRp.

DETAILED DESCRIPTION OF THE INVENTION

The present invention is directed to compounds according to Formula I:

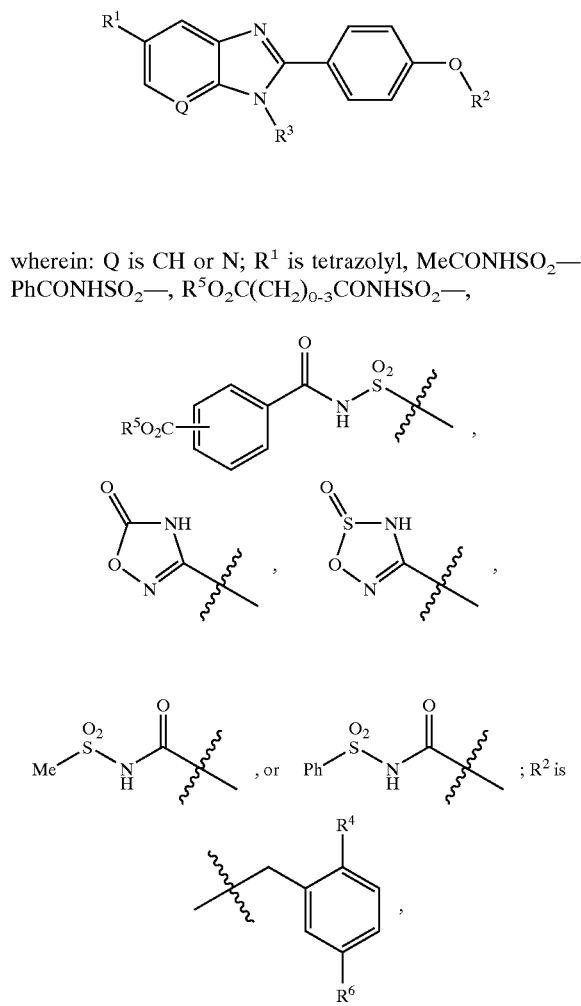

wherein: Q is CH or N; $R^1$ is tetrazolyl, MeCONHSO$_2$—, PhCONHSO$_2$—, $R^5O_2C(CH_2)_{0-3}$CONHSO$_2$—, —CH$_2$Ar$^1$, —CHPh$_2$, —CH$_2$CO(4-FPh), —CH$_2$CO(4-CF$_3$Ph), or —CH$_2$CONp where Np is naphthyl; $R^3$ is $C_{5-7}$cycloalkyl; $R^4$ is hydrogen, Ar$^2$, or Ar$^3$; Ar$^1$ is selected from the following group: phenyl, halophenyl,

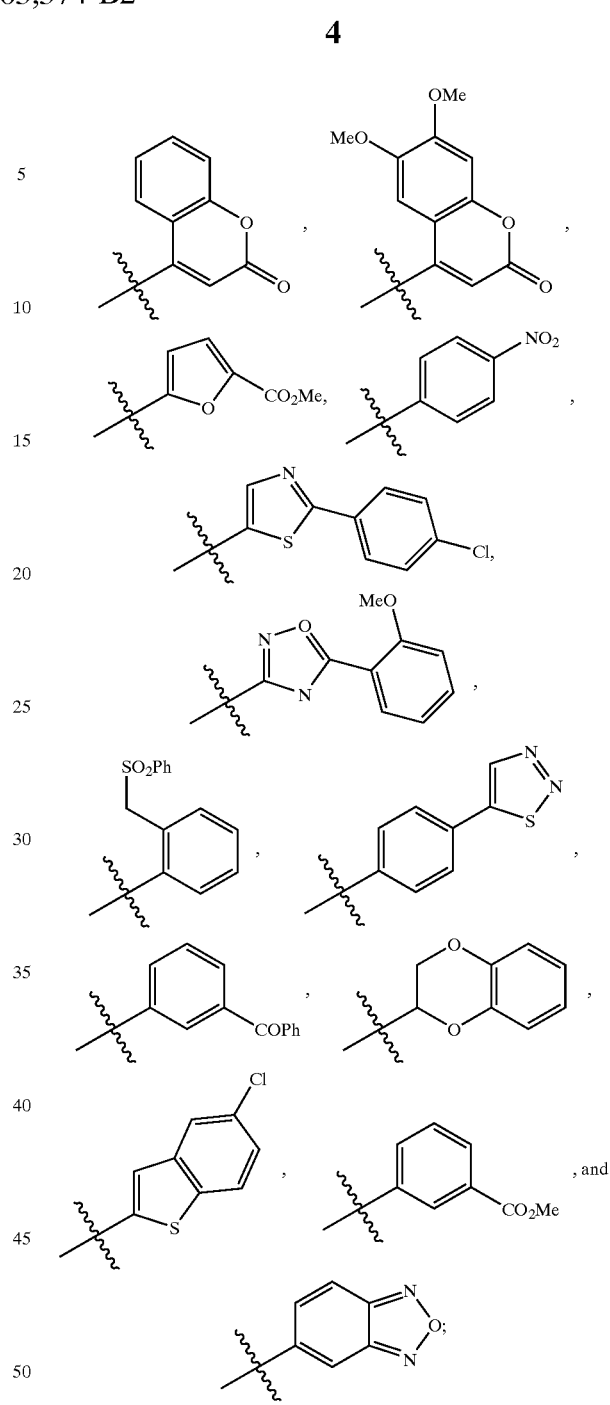

Ar$^2$ is phenyl, naphthyl, or biphenyl, optionally substituted with 1–3 substituents selected from the group comprising halogen, $C_{1-6}$ alkyl, hydroxy $C_{1-6}$alkyl, $C_{1-6}$alkoxy, $C_{1-6}$sulfoxy, $C_{1-2}$perfluoroalkyl, hydroxy, formyl, $C_{1-6}$alkylcarbonyl, cyano, nitro, $C_{1-6}$alkylamido, $CO_2R^5$, $CONR^5R^5$, $C_{1-6}$alkylsulfonamido, and dioxolane; Ar$^3$ is thienyl, furanyl, pyrrolyl, benzothiophenyl, benzofuranyl, indolyl, quinolinyl, or pyrimidinyl optionally substituted with 1–2 substituents selected from the group comprising $C_{1-6}$alkyl, formyl, acetoxy, trifluoroacetoxy, and t-butoxycarbonyl; $R^5$ is hydrogen or $C_{1-6}$alkyl; $R^6$ is halogen, methoxy, $CO_2R^5$ or $CONR^7R^8$; $R^7$ and $R^8$ are independently hydrogen, $C_{1-6}$alkyl, —CH(Me)CO$_2$R$^5$, —(CH$_2$)$_{1-3}$CO$_2$R$^5$, —(CH$_2$)$_{1-3}$CONR$^5$R$^5$, —(CH$_2$)$_{1-3}$OH,

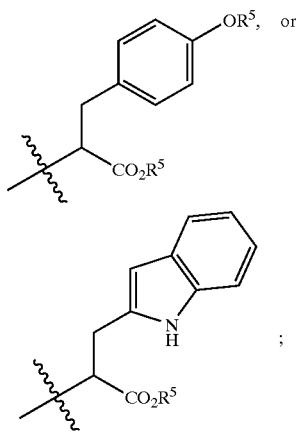

or $R^7$ and $R^8$ taken together with the nitrogen to which they are attached form pyrrolidine, morpholine, piperidine, 4-hydroxypiperidine, piperazine, or 4-methylpiperazine; or a pharmaceutically acceptable salt, solvate, or prodrug thereof.

As used herein, the following terms shall be understood to have the meaning set forth in the following definitions.

The term "compounds of the invention", and equivalent expressions, are meant to embrace compounds of formula I, and include prodrugs, pharmaceutically acceptable salts, and solvates, e.g. hydrates. Similarly, reference to intermediates, whether or not they themselves are claimed, is meant to embrace their salts, and solvates, where the context so permits.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "analog" means a compound which comprises a chemically modified form of a specific compound or class thereof, and which maintains the pharmaceutical and/or pharmacological activities characteristic of said compound or class.

The term "solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "effective amount" means an amount of a compound/composition according to the present invention effective in producing the desired therapeutic effect, i.e. inhibiting HCV.

The term "patient" includes both human and other mammals.

The term "pharmaceutical composition" means a composition comprising a compound of formula I in combination with at least one additional pharmaceutical adjuvant, excipient, vehicle or carrier component, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Any ingredient listed in Remington's Pharmaceutical Sciences, 18th ed., Mack Publishing Company, may be used.

The term "alkyl" is intended to include both branched and straight-chain saturated aliphatic hydrocarbon groups having the specified number of carbon atoms. Thus, $C_{1-6}$ alkyl refers to an alkyl group having from one to six carbon atoms. Examples of alkyl include, but are not limited to, methyl, ethyl, n-propyl, i-propyl, n-butyl, s-butyl, and t-butyl, pentyl, hexyl, heptyl and octyl.

The terms "linear and cyclic heteroalkyl" are defined in accordance with the term "alkyl" with the suitable replacement of carbon atoms with an atom such as oxygen, nitrogen or sulfur which would render a chemically stable species.

The term "heterocyclic $C_{1-6}$ alkyl group means a $C_{1-6}$ alkyl that is substituted by a heterocyclic group.

The terms "halo" or "halogen" as used herein refer to fluoro, chloro, bromo and iodo.

Alkanoyl refers to a substituent group having a $C_{1-6}$ alkyl component bonded to a carbonyl group which is then bonded to the backbone to which the substituent group is connected.

The term "alkoxy" is intended to represent an alkyl group with the indicated number of carbon atoms attached to an oxygen atom. Examples of alkoxy include, but are not limited to, methoxy, ethoxy, n-propoxy, i-propoxy, n-butoxy, s-butoxy, and t-butoxy.

The term "aryl" is intended to mean an aromatic moiety containing the specified number of carbon atoms, such as, but not limited to phenyl, indanyl or naphthyl. So $C_{6-14}$ aryl refers to an aromatic moiety having from six to fourteen carbon atoms which may be in the form of a single, bicyclic or tricyclic structure. The term "haloaryl" as used herein refers to an aryl mono, di or tri substituted with halogen atoms.

As used herein, the term "cycloalkyl" refers to a saturated monocyclic alkyl group. Examples of such carbocycles include, but are not limited to, cyclopropyl, cyclobutyl, cyclopentyl, cyclohexyl, cycloheptyl and cyclooctyl.

As used herein, the term "heterocycle" or "heterocyclic system" is intended to mean a stable 5- to 7-membered monocyclic or bicyclic or 7- to 14-membered bicyclic heterocyclic ring which is saturated, partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 2. Also included are fused ring and spiro compounds containing, for example, the above heterocycles.

The term "aromatic heterocyclic system" or "heteroaryl" means a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. The term includes any bicyclic group in which any of the above-defined heterocyclic rings is fused to a benzene ring. It is preferred that the total number of S and O atoms in the aromatic heterocycle is not more than 2.

Examples of heterocycles include, but are not limited to, piperidinyl, morpholinyl, piperazinyl, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, the disclosure of which is hereby incorporated by reference.

The compounds of the present invention are useful in the form of the free base or acid or in the form of a pharmaceutically acceptable salt thereof. All forms are within the scope of the invention.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable risk/benefit ratio.

The term "pharmaceutically acceptable prodrugs" as used herein means those prodrugs of the compounds useful according to the present invention which are, within the scope of sound medical judgment, suitable for use in contact with the tissues of humans and lower animals without undue toxicity, irritation, allergic response, and the like, commensurate with a reasonable risk/benefit ratio, and effective for their intended use, as well as zwitterionic forms, where possible, of the compounds of the invention.

The term "prodrugs", as the term is used herein, are intended to include any covalently bonded carriers which release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the skilled artisan will appreciate that the present invention encompasses prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to form the parent compound. The transformation in vivo may be, for example, as the result of some metabolic process, such as chemical or enzymatic hydrolysis of a carboxylic, phosphoric or sulphate ester, or reduction or oxidation of a susceptible functionality. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfydryl group, respectively. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups can act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p.309–396, 1985; A Textbook of Drug Design and Development, Krogsgaard-Larsen and H. Bundgaard, ed., Chapter 5; "Design and Applications of Prodrugs" p.113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, each of which is herein incorporated by reference in their entirety as though set forth in full.

The term "treating" refers to: (i) preventing a disease, disorder or condition from occurring in an animal which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

Preparation of Compounds of the Invention

Certain compounds of Formula I and intermediates used in making these compounds may exhibit tautomerism and in some cases one tautomer has been schematically drawn to represent all forms. Certain compounds of formula I can exhibit isomerism, for example geometrical isomerism, e.g., E or Z isomerism, and optical isomerism, e.g., R or S configurations. Geometrical isomers include the cis and trans forms of compounds of the invention having alkenyl moieties. It is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on HCV RdRp inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as an intermediate in preparing a pharmaceutically acceptable salt by ion exchange procedures.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and can be simply a more convenient form for use; and in practice, use of the salt form inherently amounts to use of the free acid form. The bases which can be used to prepare the base addition salts include those which produce, when combined with the free acid, pharmaceutically acceptable salts, that is, salts whose cations are non-toxic to the animal organism in pharmaceutical doses of the salts, so that the beneficial inhibitory effects on HCV RdRp inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitrites such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

Pharmaceutically acceptable salts also include quaternary lower alkyl ammonium salts. The quaternary salts are prepared by the exhaustive alkylation of basic nitrogen atoms in compounds, including nonaromatic and aromatic basic nitrogen atoms, according to the invention, i.e., alkylating the non-bonded pair of electrons of the nitrogen moieties with an alkylating agent such as methylhalide, particularly methyl iodide, or dimethyl sulfate. Quaternarization results in the nitrogen moiety becoming positively charged and having a negative counter ion associated therewith.

As will be self-evident to those skilled in the art, some of the compounds of this invention do not form stable salts. However, acid addition salts are more likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials, by techniques well known to those skilled in the art.

Compounds according to the invention, for example, starting materials, intermediates or products, are prepared as described herein or by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991; J. F. W. McOmie in "Protective Groups in Organic Chemistry" Plenum Press, 1973.

The compounds useful according to the invention optionally are supplied as salts. Those salts which are pharmaceutically acceptable are of particular interest since they are useful in administering the foregoing compounds for medical purposes. Salts which are not pharmaceutically acceptable are useful in manufacturing processes, for isolation and purification purposes, and in some instances, for use in separating stereoisomeric forms of the compounds of this invention. The latter is particularly true of amine salts prepared from optically active amines.

Where the compound useful according to the invention contains a carboxy group, or a sufficiently acidic bioisostere, base addition salts may be formed and are simply a more convenient form for use; and in practice, use of the salt form inherently amounts to use of the free acid form.

Also, where the compound useful according to the invention contains a basic group, or a sufficiently basic bioisostere, acid addition salts may be formed and are simply a more convenient form for use; and in practice, use of the salt form inherently amounts to use of the free base form.

The foregoing compounds useful according to the invention may also be combined with another therapeutic compound to form pharmaceutical compositions (with or without diluent or carrier) which, when administered, provide simultaneous administration of two or more active ingredients resulting in the combination therapy of the invention.

While it is possible for compounds useful according to the invention to be administered alone it is preferable to present them as pharmaceutical compositions. The pharmaceutical compositions, both for veterinary and for human use, useful according to the present invention comprise at lease one compound of the invention, as above defined, together with one or more acceptable carriers therefor and optionally other therapeutic ingredients. The skilled artisan will appreciate the abundance of publications setting forth the state of the art for pharmaceutical administration.

Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, dicalcium phosphate phosphate. Examples of disintegrating agents include starch, alginic acids and certain complex silicates. Examples of lubricants include magnesium stearate, sodium lauryl sulphate, talc, as well as high molecular weight polyethylene glycols.

In certain preferred embodiments, active ingredients necessary in combination therapy may be combined in a single pharmaceutical composition for simultaneous administration.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The oily phase of the emulsions of this invention may be constituted from known ingredients in a known manner. While the oily phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the emulsifying wax, and the wax together with the oil and fat make up the emulsifying ointment base which forms the oily dispersed phase of a cream formulation. Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

If desired, the aqueous phase of the cream base may include, for example, a least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogues.

The choice of suitable oils or fats for the formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used. Solid compositions may also be employed as fillers in soft and hard-filled gelatin capsules using such excipients as lactose or milk sugar as well as high molecular weight polyethylene glycols, and the like.

The pharmaceutical compositions can be administered in a suitable formulation to humans and animals by topical or systemic administration, including oral, inhalational, rectal, nasal, buccal, sublingual, vaginal, parenteral (including subcutaneous, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

A tablet may be made by compression or moulding, optionally with one or more accessory ingredients. Compressed tables may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compounds moistened with an inert liquid diluent. The tablets may optionally be coated or scored and may be formulated so as to provide slow or controlled release of the active ingredient therein.

Solid compositions for rectal administration include suppositories formulated in accordance with known methods and containing at least one compound of the invention.

If desired, and for more effective distribution, the compounds can be microencapsulated in, or attached to, a slow release or targeted delivery systems such as a biocompatible, biodegradable polymer matrices (e.g. poly(d,1-lactide co-glycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria retaining filter, or by incorporating sterilizing agents in the form of sterile solid compositions which can be dissolved in sterile water, or some other sterile injectable medium immediately before use.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds useful according to this invention administered to a host in single or divided doses may be in amounts, for example, of from about 0.0001 to about 100 mg/kg body weight daily and preferably 0.01 to 10 mg/kg/day. Dosage unit compositions may contain such amounts of such submultiples thereof as may be used to make up the daily dose. The skilled artisan will appreciate that the specific dose level for any particular patient will depend upon a variety of factors including the patient's body weight, general health, sex, diet, time and route of administration, rates of absorption and excretion, combination with other drugs and the severity of the particular disease being treated.

The amount of each component administered is determined by the attending clinicians taking into consideration the etiology and severity of the disease, the patient's condition and age, the potency of each component and other factors.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Administration of a compound of the present invention in combination with additional therapeutic agents, may afford an efficacy advantage over the compounds and agents alone, and may do so while permitting the use of lower doses of each. A lower dosage minimizes the potential of side effects, thereby providing an increased margin of safety. The combination of a compound of the present invention with such additional therapeutic agents is preferably a synergistic combination. Synergy, as described for example by Chou and Talalay, Adv. Enzyme Regul. 22:27–55 (1984), occurs when the therapeutic effect of the compound and agent when administered in combination is greater than the additive effect of either the compound or agent when administered alone. In general, a synergistic effect is most clearly demonstrated at levels that are (therapeutically) sub-optimal for either the compound of the present invention or a known antiviral agent alone, but which are highly efficacious in combination. Synergy can be in terms of improved inhibitory response without substantial increases in toxicity over individual treatments alone, or some other beneficial effect of the combination compared with the individual components.

Procedures for evaluating the biological activity of compounds or compositions according to the invention are carried out as described herein or by the application or adaptation of procedures well known in the art as described in the literature. The compounds of the present invention, their methods or preparation and their biological activity will appear more clearly from the examination of the following examples which are presented as an illustration only and are not to be considered as limiting the invention in its scope. The following examples are but preferred methods of synthesizing the compounds of the invention, which may be prepared according to any method known to the organic chemist of ordinary skill. Other features of the invention will become apparent during the following descriptions of exemplary embodiments which are given for illustration of the invention and are not intended to be limiting thereof. Each of the patents, patent applications, and other cited references, are hereby incorporated herein by reference in their entity as though set forth in full.

SYNTHESIS

The compounds of the present invention can be prepared in a number of ways well known to one skilled in the art of organic synthesis. The compounds of the present invention can be synthesized using the methods described below, together with methods known in the art of synthetic organic chemistry, or variations thereon as appreciated by those skilled in the art. A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used. In addition, it may be necessary to introduce or remove protecting groups in order to carry certain substituents through the indicated reaction conditions. A compendium of protecting groups which may be useful, together with reaction conditions for introduction and removal may be found in Greene, T. W.; Wuts, P. G. M. *Protective Groups in Organic Synthesis*, Second Edition; Wiley: New York, 1991.

The starting materials and all reagents and intermediates for these synthetic routes are either commercially available or may be prepared by methods known to one skilled in the art of organic synthesis from commercially available materials.

The following methods describe different preparations of the compounds of the present invention. The methods are often general in nature and may be used to make variations of the inventive embodiments. Other variations would be apparent to those skilled in the art.

Method A describes a general method of preparing compounds of Formula I (Scheme 1). Amine 3 is produced by nucleophilic displacement of aryl chloride 1 by cyclohexylamine (2). Reduction of the nitro group of 3 produces amine 4 which is condensed with imidate 5 to provide benzimidazole 6. The phenol of 6 can be alkylated with a variety of agents to form Formula I compounds. These agents include diphenylmethylbromide (7) which generates nitrile 8. Transformation of the nitrile moiety of 8 to a tetrazole yields 9, an example of a Formula I compound.

Additionally, the nitrile of 8 may be converted to a 5-oxo-1,2,4-oxadiazole by reaction with hydroxylamine followed by reaction with methylchloroformate or carbonyldiimidazole. The nitrile may also be converted to a 2-oxo-1,2,3,5-oxathiadiazole by reaction with hydroxylamine followed by reaction with thionyl chloride and pyridine.

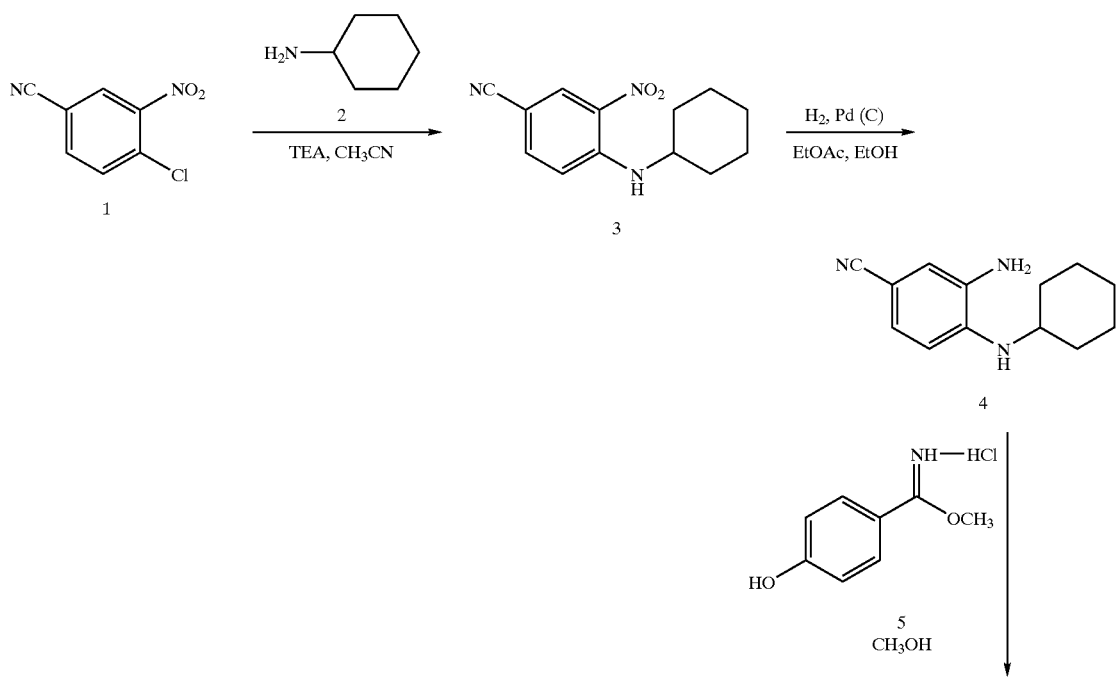

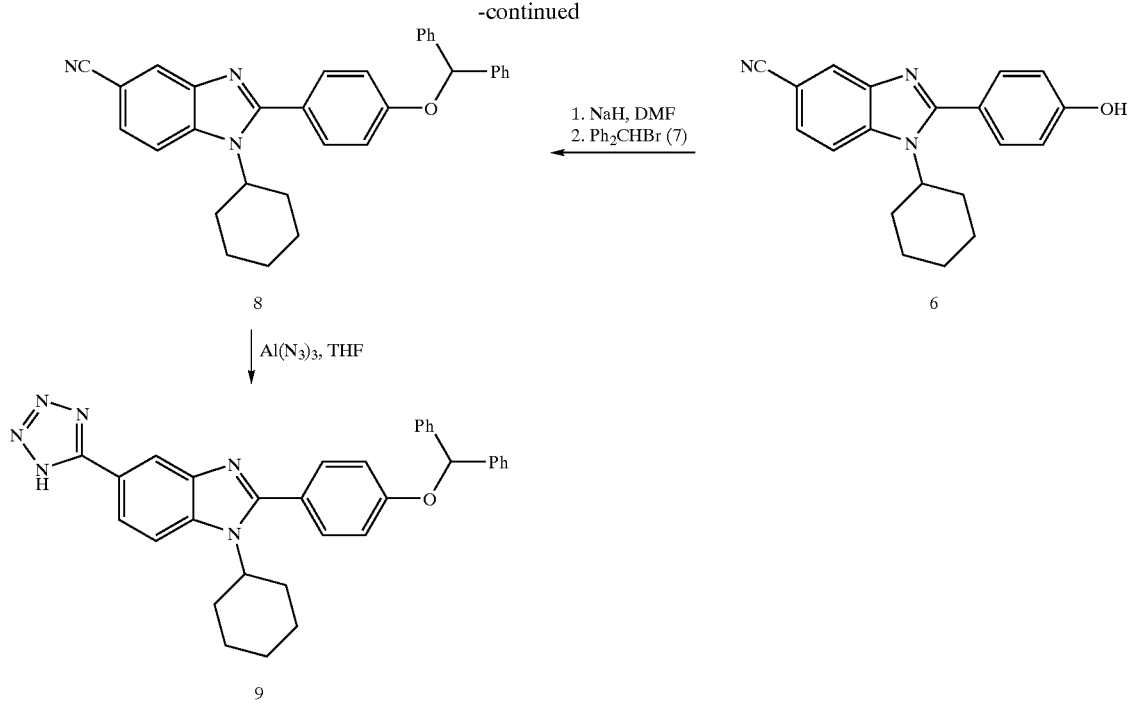

Method B provides an alternative method of preparing Formula I compounds (Scheme 2). Amine 4 can be condensed with a range of acid chlorides including 10 to form amides such as 11 which are cyclized to form benzimidazoles of which 12 is a representative example. Conversion of the nitrile moiety of 12 into a tetrazole provides compound 13, which is an example of a Formula I compound.

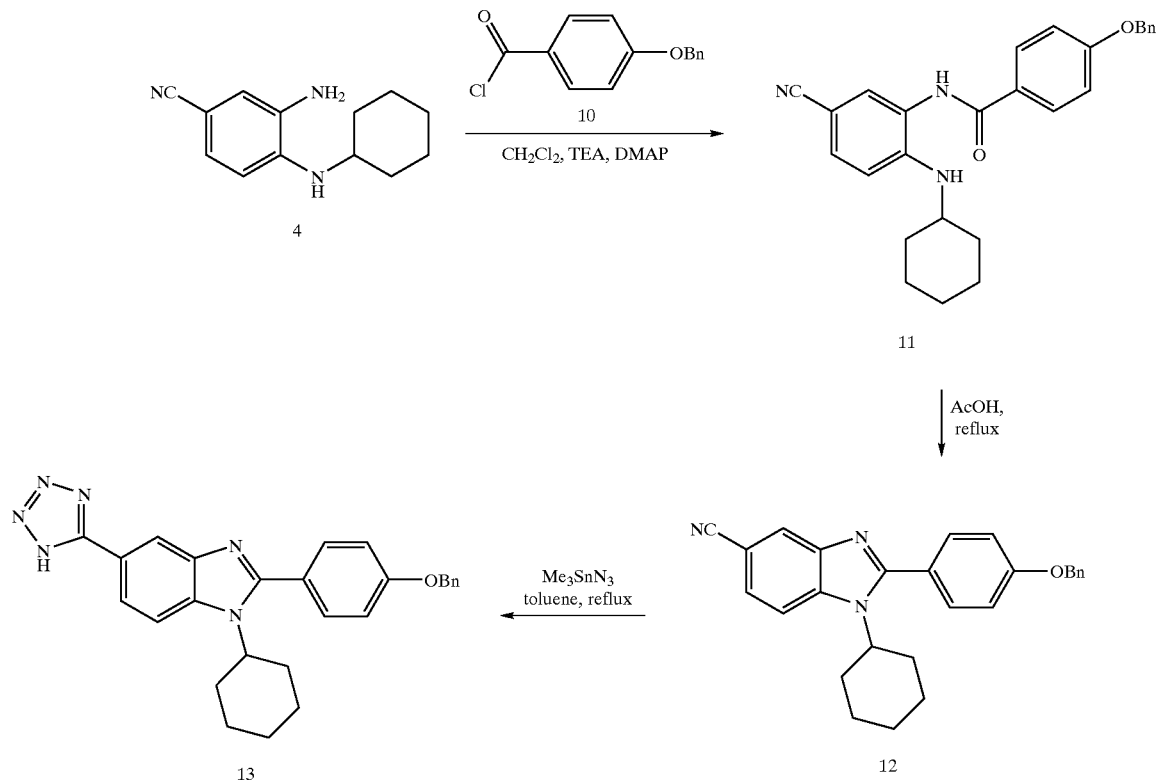

Method C describes an additional alkylative preparation of a Formula I compound. The alkylating agent 14 is prepared by coupling 4-chlorophenylboronic acid with 2-bromo-5-methoxytoluene which is in turn brominated on the tolyl methyl group. Many of the benzyl-type alkylating agents can be prepared by this route.

verted to tetrazole 21 and the tetrazole protected with a trityl group. Subsequent removal of the TBDMS protecting group with tetrabutylammonium fluoride (TBAF) affords intermediate 22 which is alkylated with a 3-bromomethyl-4-bromo benzoate ester (with, for example, R=methyl or tert-butyl). Reasonable variations of this agent (for example with a

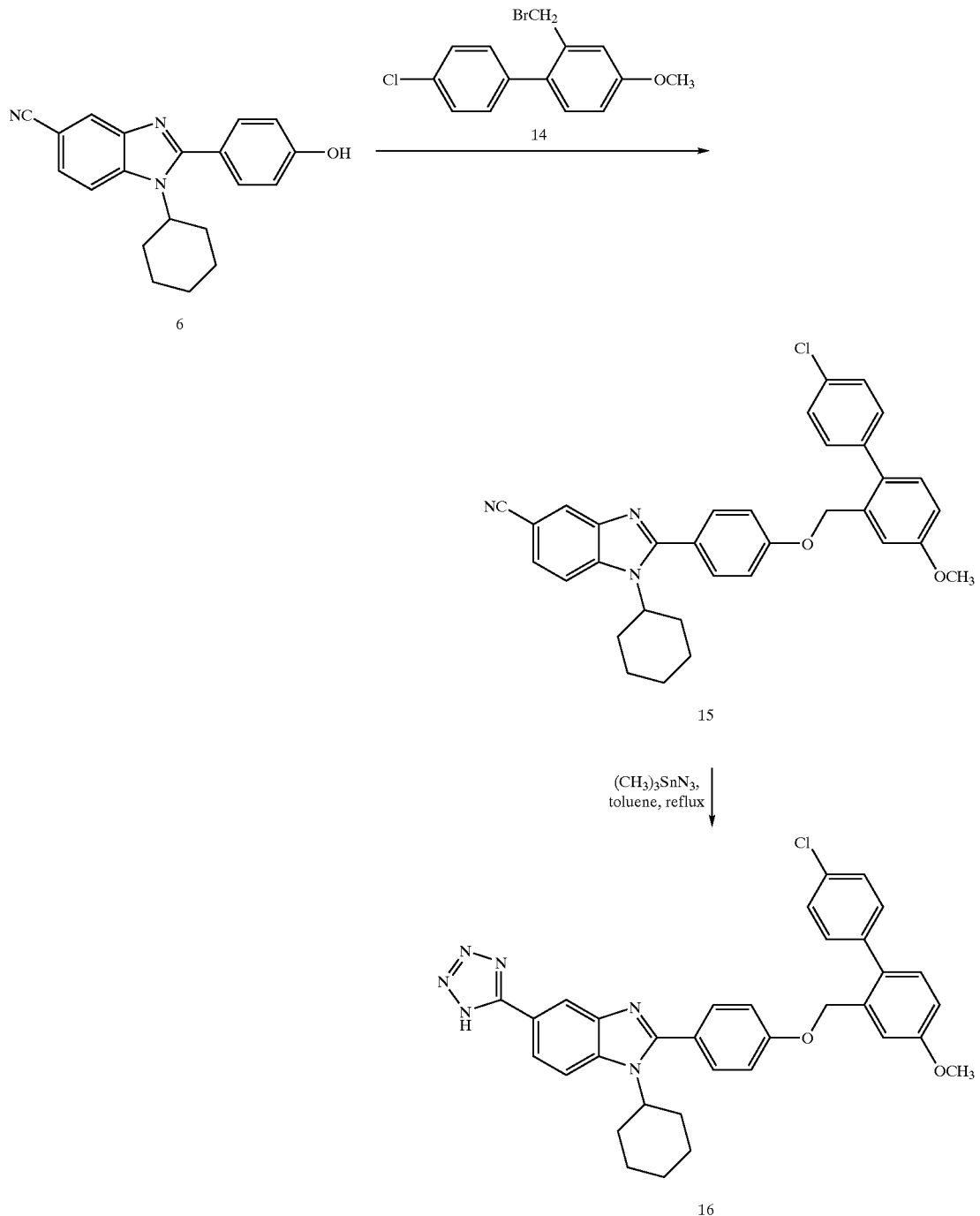

Method D provides an alternative route to Formula I compounds and describes the preparation of compounds where $R^2$ is —$CH_2C_6H_3R^4R^6$ and $R^4$ is $Ar^2$ or $Ar^3$ (Scheme 4). Phenol 6 is protected as the tert-butyldimethylsilyl (TBDMS) ether 20. The nitrile moiety of 20 is then contriflate replacing the aryl bromide or substituting a close analog of the alkyl ester) would be known to those skilled in the art. The resulting intermediate 23 may be used as a coupling partner with various organometallic compounds to afford compounds similar to 25. Trityl deprotection affords ester 26. Hydrolysis of this ester provides acids also of Formula 26 (R=H). The esters and acids are examples of Formula I compounds.
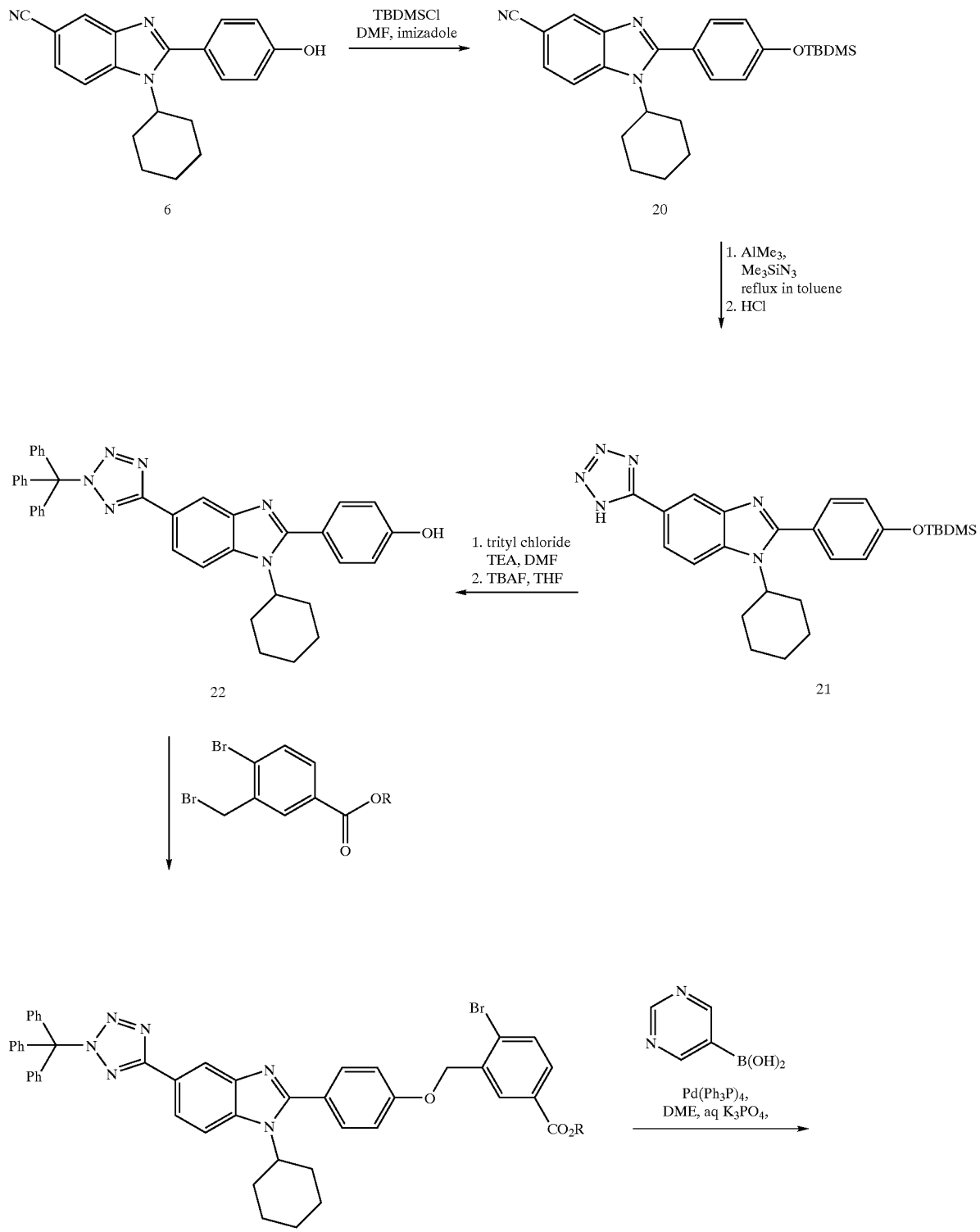

-continued

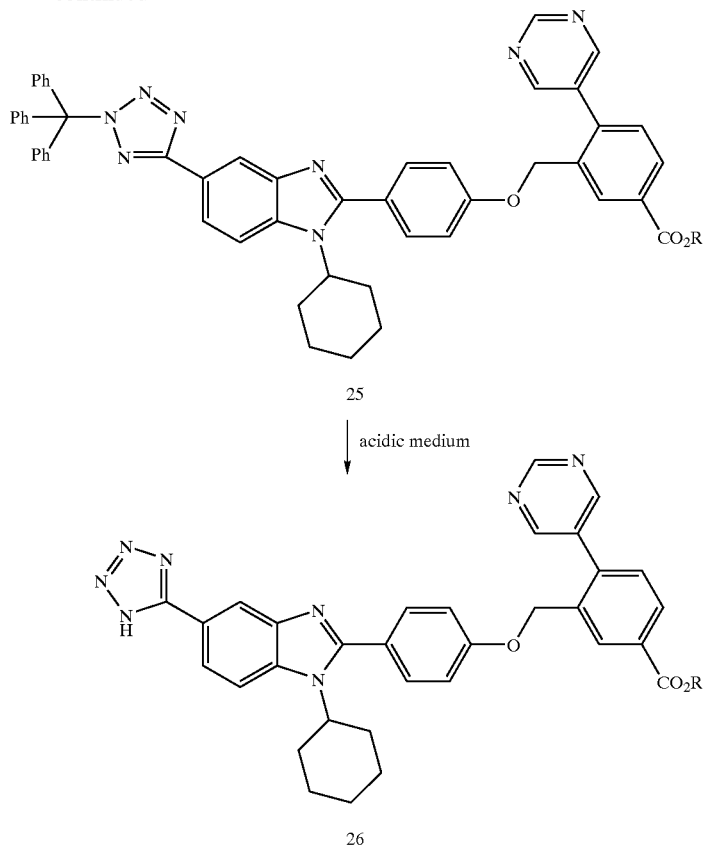

25

↓ acidic medium

26

Method E describes the use of solid phase technology for the preparation of compounds of Formula I (Scheme 5). Phenol 27 is attached to a polymeric support, such as the Merrifield resin, and converted into an appropriate linker such as 30. Intermediate tetrazole 21 is then tethered to this linker. Deprotection and alkylation as described previously provide compounds like 34a. Cleavage from the resin affords compound 34, which is an example of a Formula I compounds.

Scheme 5.

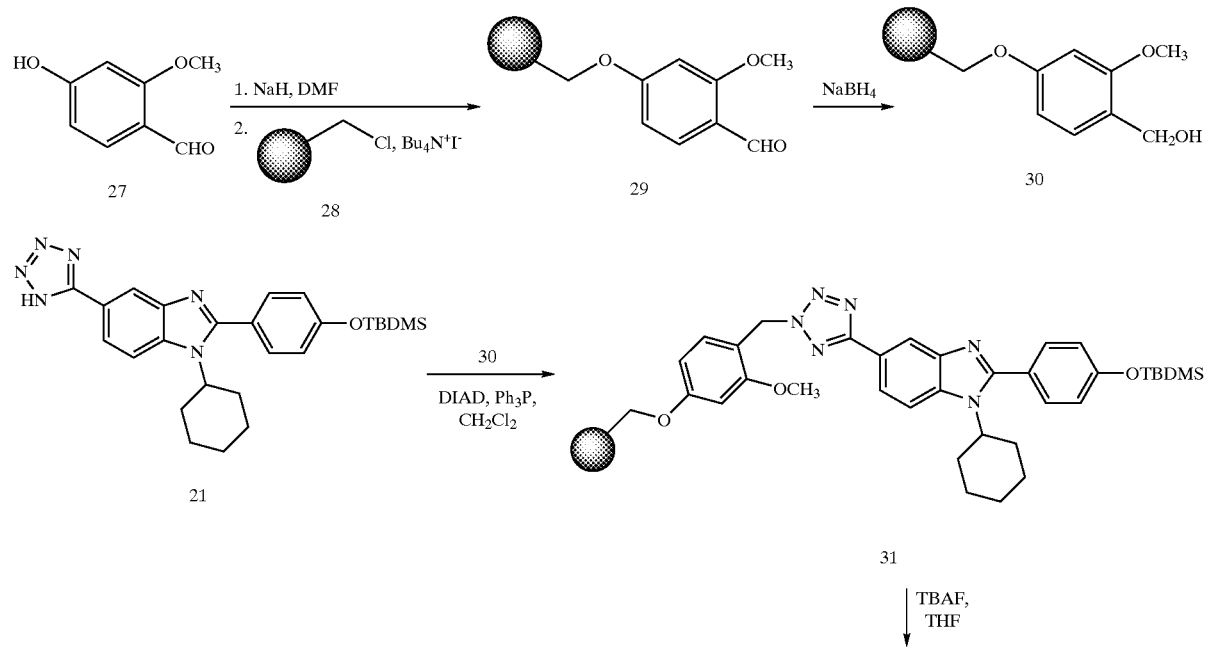

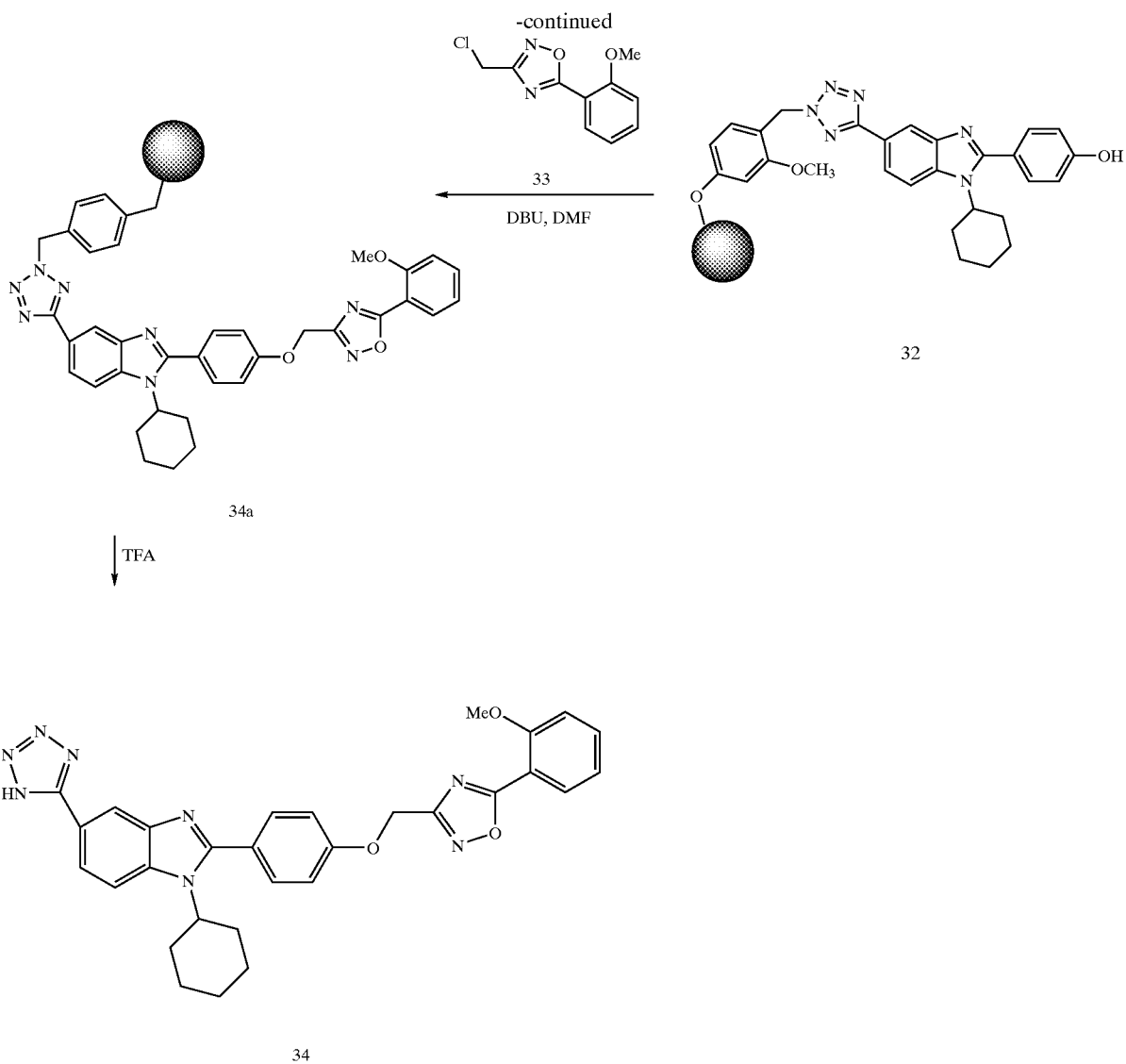
Method F provides an additional solid phase approach which utilizes chloro trityl resin 35 (scheme 6).
Scheme 6.
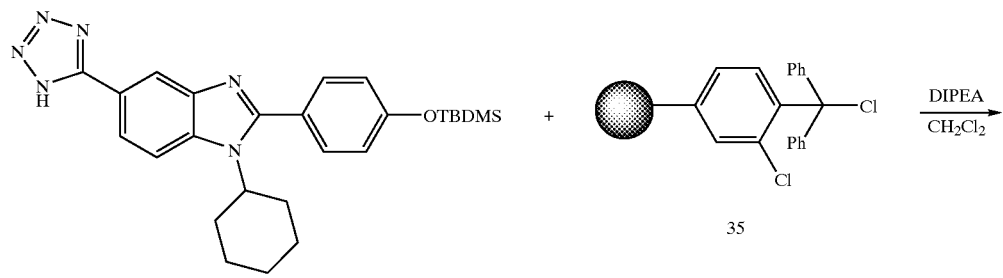

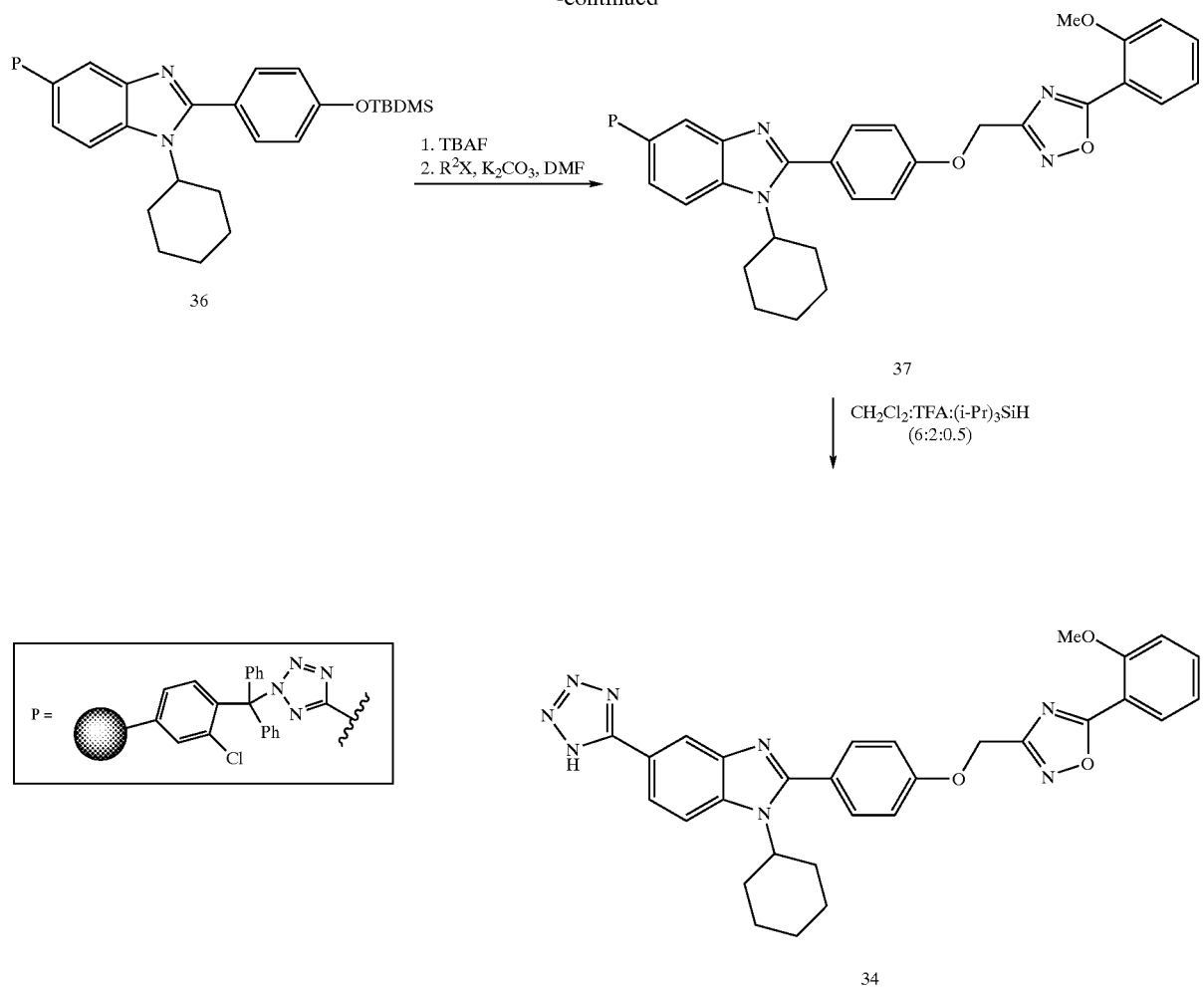

Method G provides for a preparation of Formula I compounds where $R^6$ is $CONR^7R^8$ (scheme 7). Tetrazole 23 can be coupled with a variety of organometallic compounds to afford compounds like 39. Hydrolysis of the methyl ester of 39 gives carboxylic acid 40. The carboxylic acid moiety is transformed to an amide using amines of Formula $HNR^7R^8$. In this scheme the amine is an alkyl ester of glycine, which is then hydrolyzed. The protecting group of 42 is then removed to provide compound 43. The esters, acids, and amides are examples of Formula I compounds.

Scheme 7.

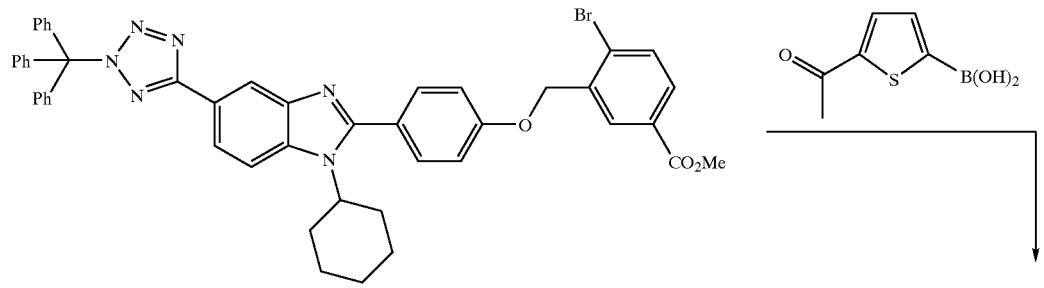

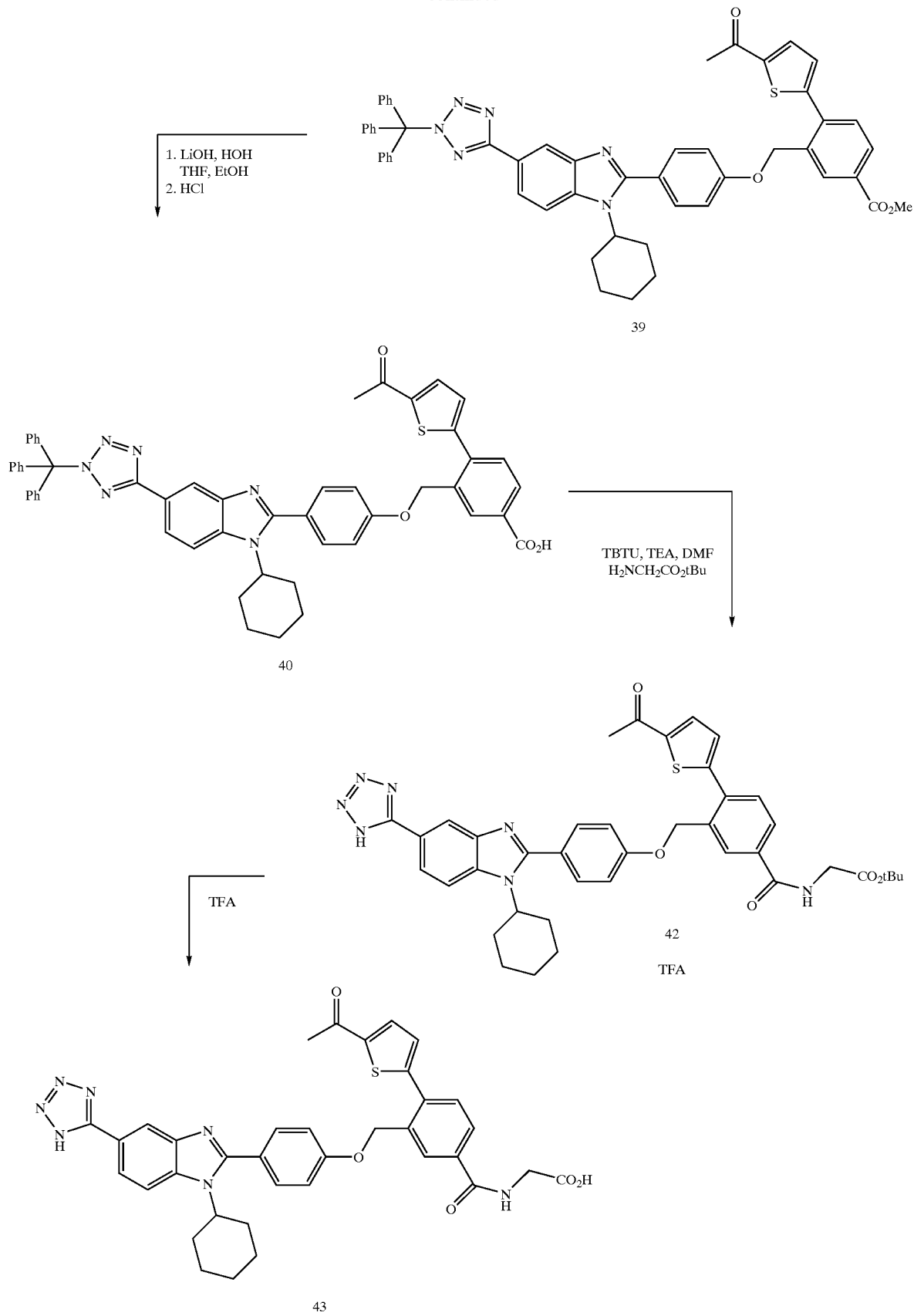

Method H provides a preparation of various $R^1$ substituents (scheme 8). Compounds of Formula 48 may be made in an analogous fashion to those of Formula 8 or 12. By judicious choice of the ester moiety of 48, ester hydrolysis may be carried out under basic (R is methyl), acidic (R is t-butyl), or neutral (R is benzyl) conditions to provide compounds like 49. Acid 49 may be coupled with a sulfonamide via the acid chloride to provide compounds like 55. In a similar manner, other acylsulfonamides provide additional examples of Formula I compounds.

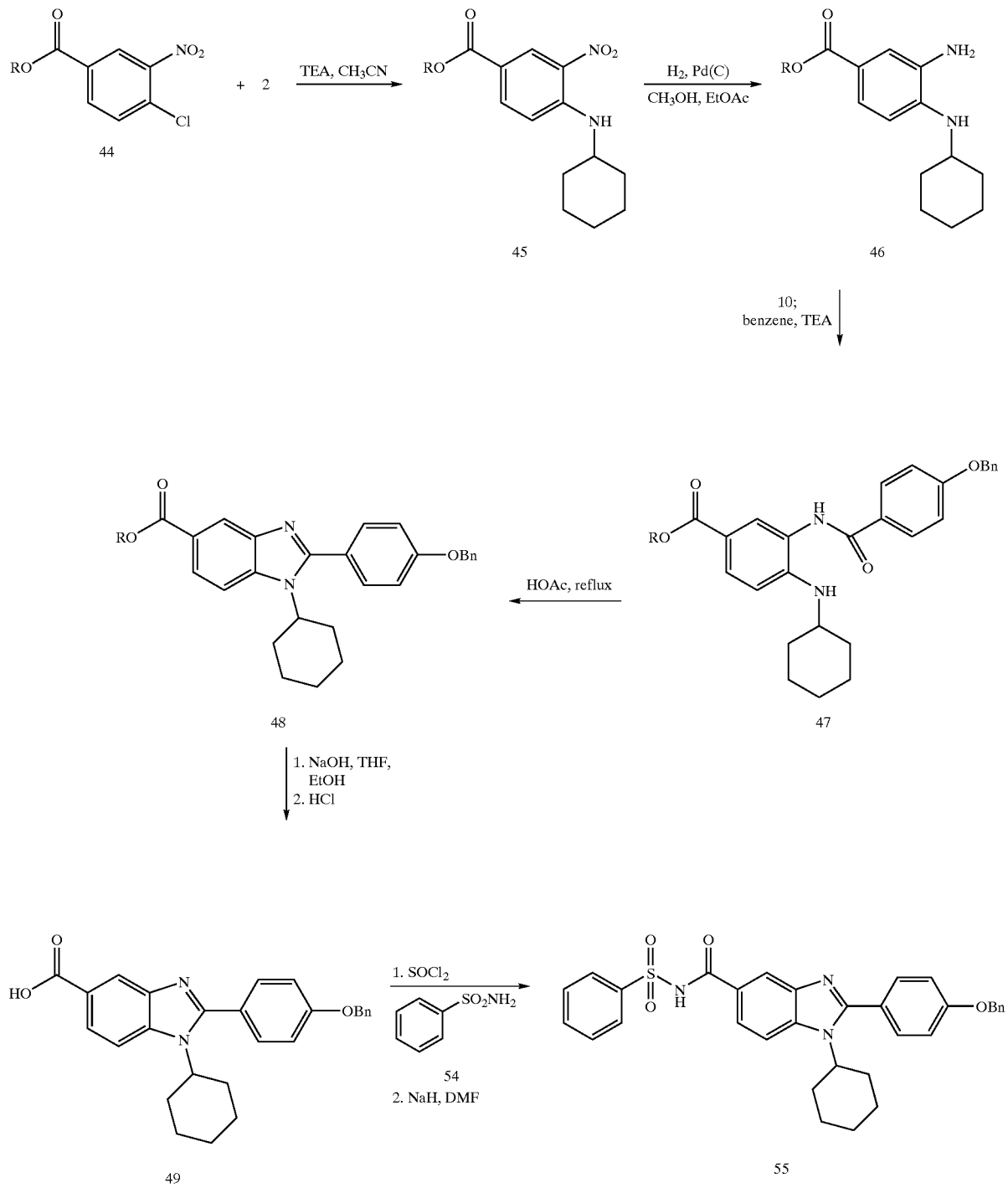

Method I provides methods for making compounds where Q is N (scheme 9). Where appropriate, these methods may be used in the previous procedures to prepare other examples of formula I compounds.
Scheme 9.
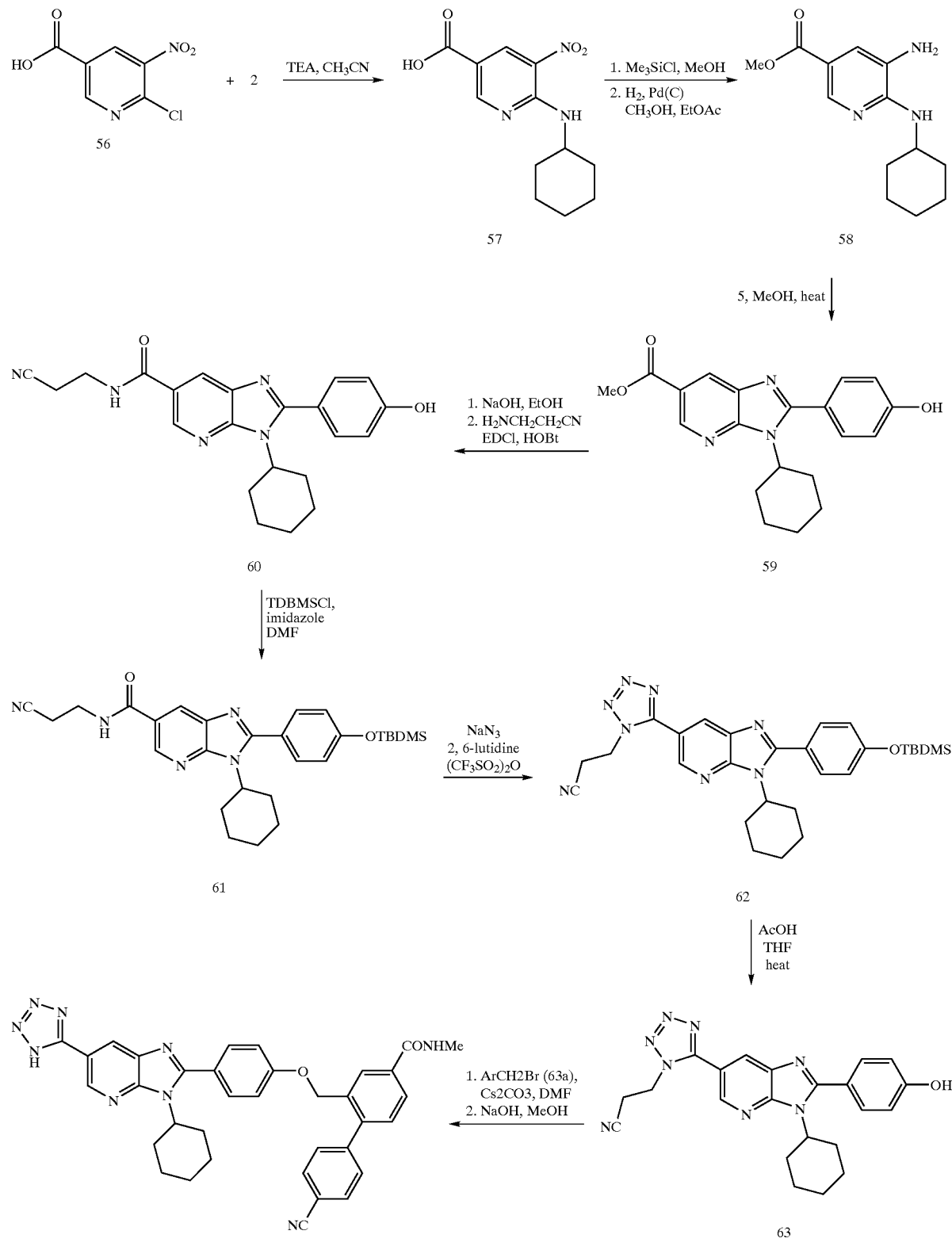

Method J provides a method for preparing Formula I compounds where $R^1$ is a $RCONHSO_2$— moiety (Scheme 10).

The preparation of the primary sulfonamide 69 follows the previous methods. Acylation of the sulfonamide can be accomplished by treating the anion of the sulfonamide with an appropriate acylating agent.

evaporative light scattering detector, "tlc" for thin layer chromatography, "v/v" for volume to volume ratio, "atm" for atmosphere, "psi" for pounds per square inch, "α", "β", "R", and "S" are stereochemical designations familiar to one skilled in the art. DMF is N,N-dimethylformamide, THF is tetrahydrofuran. Temperatures are expressed in degrees Celsius.

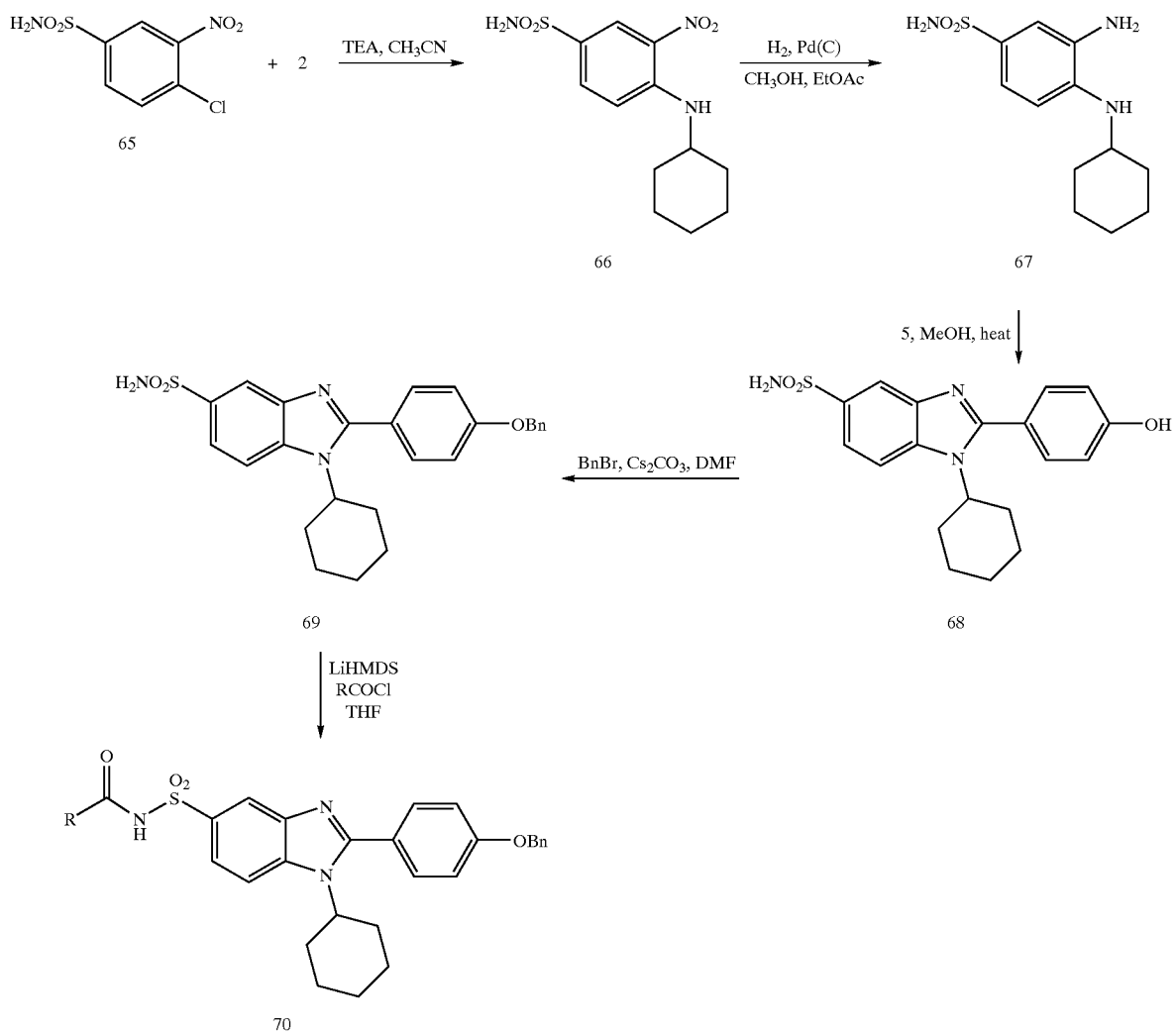

Scheme 10.

DESCRIPTION OF THE SPECIFIC EMBODIMENTS

Abbreviations used in the examples are defined as follows: "1×" for once, "2×" for twice, "3×" for thrice, "rt" for room temperature, "eq" for equivalent or equivalents, "g" for gram or grams, "mg" for milligram or milligrams, "mL" for milliliter or milliliters, "M" for molar, N for normal, "mmol" for millimole or millimoles, "min" for minute or minutes, "h" for hour or hours, "MS" for mass spectrometry, "ESI" for electrospray ionization, "NMR" for nuclear magnetic resonance spectroscopy, "$^1H$" for proton, "δ" for delta, "s" for singlet, "d" for doublet, "t" for triplet, "q" for quartet, "m" for multiplet, "br" for broad, "Hz" for hertz, "HPLC" for high pressure liquid chromatography, "ELSD" for The majority of the final compounds were purified by reverse phase chromatography using a preparative C-18 column employing gradients of methanol—water containing 0.1% of trifluoroacetic acid (TFA), and using a Shimadzu High Performance Liquid Preparative Chromatographic System employing an XTERRA 3.0×50 mm S7 column at 5 mL/min flow rate with a 2 min gradient. The final compounds were usually isolated and submitted for biological evaluations as their acid addition salts with trifluoroacetic acid. Molecular weights and purities were usually determined using a Shimadzu LCMS. NMR spectra were usually obtained on either a Bruker 500 or 300 MHz instrument.

INTERMEDIATE 3

4-(Cyclohexylamino)-3-nitrobenzonitrile (3).

A solution of 4-chloro-3-nitrobenzonitrile (5.28 g, 28.9 mmol), cyclohexylamine (5.0 mL, 43.7 mmol), and triethylamine (6.0 mL, 43.0 mL) in acetonitrile (75 mL) was stirred at 50° C. for 15 h. The reaction mixture was cooled to rt and then poured into 100 mL ice water. The solid precipitate was filtered, washed with water, and dried to afford compound 3 as a yellow solid (6.42 g, 90%). ESI-MS m/e 246.3 (M+1).

INTERMEDIATE 4

3-Amino-4-(cyclohexylamino)benzonitrile (4).

A solution of compound 3 (1.23 g, 5.01 mmol) in ethyl acetate (30 mL) and methanol (10 mL) was hydrogenated over 10% palladium on carbon (0.11 g) at 20 psi for 1 h. The reaction mixture was filtered and concentrated on a rotary evaporator to give compound 4 (1.07 g, 99%) as a red-brown solid. ESI-MS m/e 216.3 (M+1).

INTERMEDIATE 6

2-[4-Hydroxyphenyl]-1-cyclohexyl-1H-benzimidazole-5-carbonitrile (6)

A solution of ethyl 4-hydroxybenzimidate hydrochloride (5, 1.26 g, 6.7 mmol) and compound 4 (1.5 g, 5.0 mmol) in methanol (10 mL) was refluxed overnight under a nitrogen atmosphere. The reaction mixture was cooled to rt, filtered, and washed with methanol to afford 6 as a pinkish brown solid (1.26 g, 68%). ESI-MS m/e 372.1 (M+1).

INTERMEDIATE 8

2-[4-(Diphenylmethoxy)phenyl]-1-cyclohexyl-1H-benzimidazole-5-carbonitrile (8)

A 60% dispersion of sodium hydride in mineral oil (50 mg, 1.25 mmol) was added in a single portion to a stirred mixture of compound 6 in DMF (3.5 mL). When the rapid evolution of hydrogen had ceased, the mixture was cooled in an ice-water bath. Diphenylmethyl bromide (297 mg, 1.2 mmol) was added. The mixture was stirred at an oil bath temperature of 55° C. for 30 min. The mixture was cooled and poured into cold water to precipitate a solid. The solid was dried and crystallized from ethyl acetate-hexanes to afford 8 as off white needles. ESI-MS m/e 484 (M+1).

EXAMPLE 1

2-[4-(Diphenylmethoxy)phenyl]-1-cyclohexyl-5-(1H-tetrazol-5-yl)-1H-benzimidazole (9)

Aluminum trichloride (33 mg, 0.247 mmol) was added to ice cold THF (4 mL). Sodium azide (48 mg, 0.744 mmol) was added and the resulting mixture was stirred under reflux for 30 min to complete the formation of the aluminum azide. Compound 8 (100 mg, 0.206 mmol) was added and the mixture stirred under reflux for 18 h. The reaction mixture was poured into ice cold dilute HCl to precipitate a solid. The solid was dissolved in DMF (2 mL) and the solution applied to a Shimadzu Prep HPLC. The product containing fractions were combined. Removal of the methanol resulted in the precipitation of 9 as a colorless solid (22.3 mg, 20.6% yield). ESI-MS m/e 527 (M=1). $^1$H NMR (DMSO) δ 8.33 (s, 1H), 8.20 (d, 1H, J=8.6 Hz), 8.0 (1H, d, J=7.41 Hz), 7.63 (d, 2H, J=8.7 Hz), 7.55 (d, 4H, J=7.2 Hz), 7.41–7.37 (m, 4H), 7.34–7.26 (m, 4). 6.72 (s, 1H), 4.34–4.27 (m, 1H), 2.36–2.23 (m, 2H), 1.97–1.83 (m, 4H), 1.66–1.62 (m, 1H), 1.43–1.21 (m. 3H).

INTERMEDIATE 10

4-(Benzyloxy)benzoyl Chloride (10)

A solution of 4-benzyloxybenzoic acid (2.50 g, 11.0 mmol) and thionyl chloride (1.2 mL, 16 mmol) in benzene (35 mL) was refluxed for 3 h under an argon atmosphere. The reaction mixture was cooled to rt and concentrated on a rotary evaporator. The residue was re-evaporated with benzene (2x) to afford the acid chloride as a white solid.

INTERMEDIATE 11

4-(Benzyloxy)-N-[5-cyano-2-(cyclohexylamino)phenyl] benzamide (11)

A solution of the acid chloride of 4-benzyloxybenzoic acid (2.56 g, 10.4 mmol) in dichloromethane (30 mL) and dimethylformamide (5 mL) was added dropwise to a solution of compound 4 (2.23 g, 10.4 mmol) and triethylamine (2.4 mL, 17.2 mmol) in dichloromethane (15 mL). After 1.5 h, 4-dimethylaminopyridine (0.12 g) was added. The reaction was stirred at rt for 18 h and then heated to 45° C. for 4 h. The reaction was cooled to rt and then extracted with 1 N $KHSO_4$ (1x) and brine (1x). The organic layer was dried ($MgSO_4$) and concentrated on a rotary evaporator. The residue was purified by column chromatography (silica gel, 10–20% ethyl acetate/hexanes (v/v)) to afford compound 11 as a slightly purple solid (2.08 g, 47%). ESI-MS m/e 426.3 (M+1).

INTERMEDIATE 12

2-[4-(Benzyloxy)phenyl]-1-cyclohexyl-1H-benzimidazole-5-carbonitrile (12)

A solution of compound 11 (2.08 g, 4.89 mmol) in acetic acid (15 mL) was refluxed for 4.5 h. The reaction mixture was cooled to rt and concentrated on a rotary evaporator. The residue was dissolved in ethyl acetate and washed with saturated $NaHCO_3$ (2x) and water (1x). The organic layer was dried ($MgSO_4$) and concentrated on a rotary evaporator. The residue was recrystallized from hexane/ethyl acetate to give compound 12 as a tan solid (1.8 g, 90%). ESI-MS m/e 408.3 (M+1).

EXAMPLE 2

2-[4-(Benzyloxy)phenyl]-1-cyclohexyl-5-(1H-tetrazol-5-yl)-1H-benzimidazole (13)

A suspension of compound 12 (0.041 g, 0.10 mmol) and trimethyltin azide (0.023 g, 0.11 mmol) in toluene (2 mL) was refluxed for 15 h. The reaction mixture was allowed to stand at rt for 48 h. The resulting suspension was filtered and washed with toluene (2x). The solid was treated with hydrogen chloride (4 M in dioxane, several mL) for 4 h at rt. The reaction mixture was concentrated on a rotary evaporator. The residue was purified by reverse phase HPLC (C18 column, water/acetonitrile gradient containing 0.05% trifluoroacetic acid) to afford 13 as a white solid (0.009 g, 20%). $^1$H NMR ($CDCl_3$) δ 8.22 (br s, 1H), 8.05 (br m, 1H), 7.82 (br m, 3H), 7.52–7.38 (m, 5H), 7.30 (br m, 2H), 5.23 (s, 2H), 4.53 (br m, 1H), 2.27 (br m, 4H), 2.06 (br m, 2H), 1.84 (br m, 1H), 1.40 (br m, 3H); ESI-MS m/e 451.3 (M+1); HPLC purity (ELSD)>95%.

INTERMEDIATE 14

4'-Chloro-2-methyl-1,1'-biphenyl-4-yl)methyl ether (2 Steps)

(Step 1) A solution of 4-bromo-3-methylanisole (6.48 g, 32.2 mmol), 4-chlorophenyl-boronic acid (6.02 g, 38.5 mmol), tri-o-tolyl phosphine (0.98 g, 3.2 mmol), and $NaHCO_3$ (11.0 g, 130.9 mmol) in ethylene glycol dimethyl ether (100 mL) and water (33 mL) was degassed with a stream of nitrogen for 20 min. Palladium (II) acetate (0.361 g, 1.6 mmol) was added under a nitrogen atmosphere. The reaction mixture was heated at 90° C. for 2 h. The mixture was cooled to rt, and the organic layer was washed with water (1×), brine (1×), dried (MgSO$_4$) and concentrated on a rotary evaporator. The residue was suspended in hexane and filtered. The filtrate was concentrated and purified by column chromatography (silica gel, eluting with hexanes, followed by 10% ethyl acetate/hexane (v/v) to give the product as a clear oil (5.2 g, 70%). ESI-MS m/e 233.1 (M+1).

2-(Bromomethyl)-4'-chloro-4-methoxy-1,1'-biphenyl (14)

(Step 2) A solution of the previous product(5.2 g, 22.3 mmol), N-bromosuccinimide (4.12 g, 23.1 mmol), AIBN (0.183 g, 1.11 mmol) in carbon tetrachloride (100 mL) was refluxed for 1 h. The mixture was cooled to rt, filtered through a silica plug and concentrated on a rotary evaporator. The residue was dissolved in hexane and cooled in an ice bath. The white crystals were filtered to give 14 (3.6 g, 52%). ESI-MS m/e 311.1(M+1).

INTERMEDIATE 15

2-{4-[(4'-Chloro-4-methoxy-1,1'-biphenyl-2-yl)methoxy]phenyl}-1-cyclohexyl-1H-benzimidazole-5-carbonitrile (15)

A suspension of compound 6 (0.330 g, 1.04 mmol) in DMF (2.4 mL) and cesium carbonate (339 mg, 1.04 mmol) was heated at 40° C. until almost clear. Compound 14 (356 mg, 1.14 mmol) was added in portions. The reaction mixture was stirred at rt for 18 h. The mixture was concentrated on a rotary evaporator. The residue was washed with water and collected by filtration. This material was purified by column chromatography (silica gel, 50% to 100% hexane/ethyl acetate (v/v) to give compound 15 (0.55 g, 100% yield). ESI-MS m/e 548 (M=1).

EXAMPLE 3

2-{4-[(4'-Chloro-4-methoxy-1,1'-biphenyl-2-yl)methoxy]phenyl}-1-cyclohexyl-5-(1H-tetrazol-5-yl)-1H-benzimidazole (16)

Compound 15 (0.110 g, 0.20 mmol) was converted to compound 16 (0.012 g, 10%) by the same method used in example 2. $^1$H NMR (CDCl$_3$) δ 8.18 (br s, 1H), 7.98 (d, 2H, J=8.7 Hz), 7.67 (d, 2H, J=8.8 Hz), 7.36–7.18 (m, 7H), 7.11 (d, 1H, J=2.6 Hz), 6.92 (dd, 1H, J=2.9, 8.5 Hz), 6.81 (d, 2H, J=8.4 Hz), 4.85 (s, 2H), 4.25 (br m, 1H), 3.38 (s, 3H), 2.28 (br m, 4H), 2.05 (br m, 2H), 1.80 (br m, 1H), 1.35 (br m, 3H); ESI-MS m/e 591.2 (M+1); HPLC purity (UV)>95%.

INTERMEDIATE 20

2-[4-(tert-Butyldimethylsilyoxy)phenyl]-1-cyclohexyl-1H-benzimidazole-5-carbonitrile (20)

Imidazole (2.72 g, 0.040 mol) and tert-butyldimethylchloro silane (2.89 g, 192 mmol) were added to a stirred solution of compound 6 (5.1 g, 16 mmol) in DMF (10 mL). Stirring was continued for 15 h at 100° C. Upon cooling 20 crystallized. The crystals were collected and washed with ethyl acetate followed by water. The yield of 20 (after drying) was 4.70 g (62%).

INTERMEDIATE (21)

2-[4-(tert-Butyldimethylsilyoxy)phenyl]-1-cyclohexyl-5-(1H-tetrazol-5-yl)-1H-benzimidazole (21)

Trimethylaluminum (20 mL of a 2.0 M solution in toluene, 0.040 mol) was added to a dry flask. Azidotrimethylsilane (5.3 mL, 0.040 mol) and compound 20 were added. The solution was stirred for 18 h at an oil bath temperature of 95° C. The solution was cooled and poured into a mixture of ethyl acetate and ice. The solution was carefully acidified with dilute hydrochloric acid (caution-done in hood, hydrazoic acid liberated) to precipitate compound 21. The compound was crystallized from ethyl acetate—hexanes to afford 21 as a pinkish solid (4.13 g, 87%).

INTERMEDIATE 22

2-[4-Hydroxyphenyl]-1-cyclohexyl-5-[2-(trityl)-2H-tetrazol-5-yl]-1H-benzimidazole (22)

Trityl chloride (4.57 g, 0.0164 mol) and N,N-diisopropylethylamine (2.42 g, 0.0187 mol) were added to a stirred mixture of compound 21 (7.4 g, 0.0156 mol) in DMF (36 mL). The mixture was stirred for 18 h at an oil bath temperature of 70° C. The mixture was cooled and poured into a mixture of ethyl acetate and water to precipitate the fully protected benzimidazole, 2-[4-(tert-butyldimethylsilyoxy)phenyl]-1-cyclohexyl-5-[2-(trityl)-2H-tetrazol-5-yl]-1H-benzimidazole. The solid was collected, washed with cold water and dried to afford the protected benzimidazole as a colorless solid (9.1 g, 81% yield). ESI-MS m/e 717 (M+1). HPLC purity (uv) 94%.

An additional 770 mg was obtained from the ethyl acetate layer after concentration on a rotary evaporator.

A 1M solution of tetrabutylammonium fluoride in THF (34 mL, 0.034 mol) was added in one portion to stirred mixture of the fully protected benzimdazole (9.8 g, 0.0137 mol) in THF (100 mL). The mixture was stirred at rt for 40 min when acetic acid (2.0 mL) was added. Stirring was continued for an additional 5 min. The mixture was poured into ethyl acetate-water. The organic layer was washed (water, dilute sodium bicarbonate, and brine) and partially concentrated on a rotary evaporator. Diethyl ether was added to the resulting slurry to fully precipitate 22 as a pinkish solid (8.2 g, 100% yield). ESI-MS M/e 603 (M+1).

Methyl 4-bromo-3-(bromomethyl)benzoate

A stirred mixture of methyl 4-bromo-3-methylbenzoate (25.0 g, 0.109 mol) in carbon tetrachloride (250 mL) was warmed to near boiling when N-bromosuccinimide 21.4 g, 0.12 mol) and 2,2'-azobisisobutyronitrile (250 mg) were added. The mixture was stirred under reflux for 18 h, during which time it was irradiated with a 200W light bulb. The mixture was cooled and filtered to remove the succinimde. Partial concentration on a rotating evaporator resulted in crystallization of the methyl ester (18.4 g, 73.7% yield). $^1$H NMR (CDCl$_3$)δ 8.10 (s, 1H), 7.81 (d, 1H, J=8 Hz), 7.64 (d, 1H, J=8 Hz), 4.61 (s, 2H), 3.95 (s, 3H).

tert-Butyl 4-bromo-3-(bromomethyl)benzoate

A suspension of 4-bromo-3-methylbenzoic acid (10 g, 46.5 mmol) was heated to 80° C. and N,N-dimethylformamide di-tert-butyl acetal (44.6 mL, 186.0 mmol) was added dropwise over 30 minutes under a nitrogen atmosphere; stirring was continued at this temperature for 1.5 h. The reaction mixture was allowed to cool and then washed with water (1×), saturated NaHCO$_3$ (1×), and brine (1×). The organic layer was dried (Na$_2$SO$_4$) and concentrated to afford tert-Butyl 4-bromo-3-methylbenzoate (as an off-white oil (8.8 g, 70%). ESI-MS m/e 311.9 (M+CH$_3$CN+1).

A stirred mixture of ten-butyl 4-bromo-3-methylbenzoate (25.0 g, 0.116 mol) in carbon tetrachloride (250 mL) was heated to near boiling when N-bromosuccinimide (18.34 g, 0.103 mol) and 2,2'-azobisisobutyronitrile (358 mg) were added. The mixture was stirred under reflux for 18 h. The succinimide was removed by filtration and the filtrate concentrated on a rotary evaporator. The residue was chromatographed on silicic acid (300 g), using the flash technique and eluting with hexanes to afford the product as a pale yellow oil (25.4 g, 77% yield) which eventually crystallized. $^1$H NMR (CDCl$_3$) δ 8.03 (s, 1H), 7.73 (d, 1H, J=8 Hz), 7.61 (d, 1H, J=8 Hz), 7.25 (s, 1H), 4.61 (s, 2H), 1.599 (s, 9H).

INTERMEDIATE 23

(R=Methyl)

Methyl 4-Bromo-3-[[4-[1-cyclohexyl-5-(triphenylmethyl)-2H-tetrazol-5-yl]1-H-benzimidazol-2-yl]phenoxy]methyl]benzoate A mixture of compound 22 (400 mg, 0.68 mmol) and potassium carbonate (282 mg, 2.04 mmol) in DMF (10 mL) was stirred at rt for 10 min. Methyl 4-bromo-3-(bromomethyl)benzoate (230 mg, 0.75 mmol) was added and stirring was continued for 18 h at 80° C. The mixture was poured into ethyl acetate-water. The aqueous layer was re-extracted with ethyl acetate. The organic layers were combined and washed (water, brine) and dried over sodium sulfate. The solution was concentrated on a rotary evaporator. The residue was purified by flash chromatography on silicic acid and eluting with hexanes-ethyl acetate to afford 23 (R=methyl) as a colorless oil (400 mg, 71% yield) which eventually crystallized. ESI-MS m/e 83 (M+1) $^1$H NMR (CDCl$_3$) δ 8.55 (s, 1H), 8.25 (s, 1H), 8.05 (d, 1H, J=8 Hz), 7.86 (d, 1H, J=8 Hz), 7.68 (d, 2H, J=8.5 Hz), 7.61 (d, 2H, J=8.5 Hz), 7.33 (m, 10H), 7.18 (m, 6H), 7.15 (s, 1H), 5.22 (s, 2H), 4.38 (m, 1H), 3.91 (s, 3H), 2.30 (m, 21H), 1.95 (m, 4H), 1.75 (m, 2H), 1.34 (m, 3H).

INTERMEDIATE 23

(R=tert-butyl)

4-Bromo-3-[[4-[1-cyclohexyl-5-(triphenylmethyl)-2H-tetrazol-5-yl]-1H-benzimidazol-2-yl]phenoxy]methyl]-benzoic acid 1,1-dimethylethyl ester (23)

A mixture of compound 22 (2.04 g, 3.88 mmol) and cesium carbonate (1.38 g, 4.23 mmol) in DMF (20 mL) was stirred at rt for 10 min. tert-Butyl 4-bromo-3-(bromomethyl) benzoate (1.24 g, 3.55 mmol) was added and stirring continued for 18 h at rt. The mixture was poured into ethyl acetate-cold water. The organic layer was washed (water, brine), dried (MgSO$_4$), and concentrated on a rotary evaporator. The residue was crystallized from ethyl acetate-hexanes to afford 23 (R=tert-butyl) (2.3 g, 78% yield). ESI-MS m/e 872 (M+1).

INTERMEDIATE 25

3-[[4-[1-Cyclohexyl-5-[2-(triphenylmethyl)-2H-tetrazol-5-yl]-1H-benzimidazol-2-yl]phenoxymethyl]-4-(5-pyrimidinyl)-benzoic acid 1,1-dimethylethyl ester (25)

A solution of compound 23 (215 mg, 0.25 mmol) and pyrimidine-5-boronic acid (24, 37 mg, 0.29 mmol) in dimethoxyethane (3.5 mL) was degassed at rt with a stream of nitrogen. Tetrakis(triphenylphosphine)palladium(0) (29 mg, 0.025 mmol) was added, followed by a degassed solution of potassium phosphate (315 mg, 1.48 mmol) in water (0.22 mL). The contents of the sealed vial were shaken at 90° C. for 18 h on an Innova platform shaker mounted with a Thermolyne Dri-Bath heater. The vial was cooled and the contents poured into a mixture of methylene chloride and water. The organic layer was washed 2× with water followed by brine. The organic layer was dried over sodium sulfate and crude 25 isolated as a froth after concentration on a rotating evaporator.

EXAMPLE 4

3-[[4-[1-Cyclohexyl-5-(1H-tetrazol-5-yl)-1H-benzimidazol-2-yl]phenoxy]methyl]-4-(5-pyrimidinyl)benzoic acid (26, R=H)

A solution of 4N hydrochloric acid in dioxane (1.5 mL) was added to a vial containing crude 25 (40 mg). The mixture was sonicated for 2 h. Dilution with diethyl ether precipitated crude 26 (30 mg) which was collected, washed with ether and dried. A solution of 26 in DMF was purified by preparative HPLC to afford 26 as an acid addition salt with trifluoroacetic acid (1.9 mg, 6.6% yield). ESI-MS m/e573 (M+1). Purity 98%(uv) by HPLC

INTERMEDIATE 29

Resin bound 4-Hydroxy-2-methoxybenzaldehyde (29)

A solution of 4-hydroxy-2-methoxybenzaldehyde (45.6 g, 0.30 mol) in DMF (70 mL) was added dropwise to a cooled ice/water bath and stirred mixture of 95% sodium hydride (7.58 g, 0.03 mol) in DMF (200 mL). After the vigorous evolution of hydrogen had subsided, a catalytic amount (60 mg) of tetrabutylammonium iodide was added followed by Merrifield resin (60 g of 100–200 mesh containing 1.25 mmol/g). The cooling bath was removed and stirring continued at an oil bath temperature of 65° C. for 15 min when the reaction mixture set solid. It was diluted with additional DMF (250 mL) and stirring continued for an additional 20 h. The mixture was cooled and the solid collected and washed sequentially with DMF (2×100 mL), water (3×150 mL), DMF:water (1:1, 2×100 mL), DMF (2×100 mL), methanol (3×100 mL), methylene chloride (2×100 mL), and methanol (3×100 mL). The bound aldehyde was dried over phosphorous pentoxide for 24 hr at 0.1 mm to afford 68.5 g of 29 (100% yield) with a loading of about 1.24 mmol/g.

INTERMEDIATE 30

Resin bound 4-Hydroxy-2-methoxybenzyl alcohol (30)

Sodium borohydride (10.0 g, 0.26 mol) was added to a mixture of compound 29 (35 g, 0.044 mol) in 250 mL of a 1:1 mixture of THF and 95% ethyl alcohol. The mixture was shaken for 18 h at rt. The resin was washed sequentially with DMF (100 mL), water (100 mL), DMF (100 mL), methanol (100 mL), and methylene chloride (100 mL). This latter washing sequence was repeated (3×). The resin was dried in vacuo to afford 30 as a colorless solid (33.9 g), with an approximate loading of 1.25 mmol/g. An IR spectrum of 30 was negative for an aldehyde carbonyl peak.

INTERMEDIATE 31

Resin bound 2-[4-(tert-Butyldimethylsilyoxy)phenyl]-1-cyclohexyl-5-(2H-tetrazol-5-yl)-1H-benzimidazole (31)

Compound 21 (4.13 g, 8.7 mmol), diisopropylazodicarboxylate (2.07 mL, 10.5 mmol) and triphenylphosphine (2.75 g, 10.5 mmol) were added to a suspension of resin 30 (2.8 g, 3.5 mmol) in a 1:1 mixture of THF and methylene chloride (50 mL) at 0° C. The mixture was allowed to reach rt, and was shaken for 18 h and filtered. The resin was washed successively with DMF (2×50 mL), 1:1 DMF-water (50 mL), DMF (2×50 mL), methanol (3×50 mL), and methylene chloride (3×50 mL). The resin was dried in vacuo to afford 2.65 g of 31.

INTERMEDIATE 32

Resin bound 2-[4-hydroxyphenyl]-1-cyclohexyl-5-(2H-tetrazol-5-yl)-1H-benzimidazole (32)

Compound 31 (2.65 g, 3.3 mmol) was added to tetrabutylammonium fluoride (17.5 mL of a 1.0 N solution in THF, 17.5 mmol) at rt. The suspension was shaken for 66 h and was filtered. The resin was washed and dried as described in the preceding experiment to afford resin bound 2-[4-hydroxyphenyl]-1-cyclohexyl-5-(2H-tetrazol-5-yl)-1H-benzimidazole (2.5 g).

EXAMPLE 5

1-Cyclohexyl-2-[4-[5-(2-methoxyphenyl)-1,2,4-oxadiazol-3-ylmethoxy]phenyl]-5-[1H-tetrazol-5-yl]-1H-benzimidazole (34)

Compound 32 (50 mg, 0.06 mmol) 3-chloromethyl-5-(2-methoxyphenyl)-1,2,4-oxadiazole (67 mg, 0.30 mmol), and 1,8-diazabicyclo[5.4.0]undec-7-ene (DBU, 46 mg, 0.3 mmol) were added to DMF (1.0 mL) in a fritted vial. The vial was shaken at rt for 18 h in a Bodan MiniBlock™ II reactor. The resin was filtered and washed successively with DMF (1 mL), water (1 mL), DMF (2×1 mL), methyl alcohol (3×1 mL), and methylene chloride (3×1 mL). The vial was recharged with 1 mL of TFA:methylene chloride (95:5) and was shaken for 18 h at rt. The contents of the vial were filtered and the filtrate concentrated to dryness using a Speed Vac® Plus. The residue was dissolved in DMF and the solution purified by preparative HPLC to afford 34 as a salt with TFA (0.7 mg, 1.8% yield).

INTERMEDIATE 36

Resin Bound 2-[4-(tert-Butyldimethylsilyoxy)phenyl]-1-cyclohexyl-5-(1H-tetrazol-5-yl)-1H-benzimidazole (36)

The chlorotrityl resin (2.5 g of 200–400 mesh containing 1.14 mmol/g) was added to dry methylene chloride (25 mL) in a resin flask and under argon. Disopropylethylamine (1.47 g, 0.0115 mol) and compound 21 (5.41 g, 0.0114 mol) were added. The mixture was shaken for 4 h. The resin was collected and successively washed with methylene chloride (3×50 mL), methanol (2×50 mL), and methylene chloride (2×50 mL). The resin was collected and dried to afford 36 (4.8 g).

INTERMEDIATE 37

Resin bound 1-Cyclohexyl-2-[4-[5-(2-methoxyphenyl)-1,2,4-oxadiazol-3-ylmethoxy]phenyl]-5-[2H-tetrazol-5yl]-1H-benzimidazole (37)

The protected tetrazole 36 (4.8 g) was suspended in THF (70 mL). A solution of TBAF (28 mL of 1.0 N, ca 5 eq) was added and the mixture shaken for 5 h at rt. The resin was collected and washed successively with THF (70 mL), methylene chloride (2×70 mL), methanol (2×70 mL), and methylene chloride (2×70 mL). The resin was collected and dried to afford the desilylated intermediate (3.8 g).

The desilylated resin (100 mg, 0.12 mmol), 3-chloromethyl-5-(2-methoxyphenyl)-1,2,4-oxadiazole (81 mg, 0.36 mmol), potassium carbonate (50 mg, 0.27 mmol), and sodium iodide (18 mg, 0.12 mmol) were added to a vial containing DMF (1.0 mL). The mixture was shaken at 75° C. for 18 h. The resin was collected and was washed successively with DMF (2×2 mL), DMF-70% water (2×2 mL), DMF (2 mL), methanol (2 mL), and methylene chloride (2×2 mL). The resin was dried to afford 37 which was directly cleaved to afford 34.

1-Cyohexyl-2-[4-[5-(2-methoxyphenyl)-1,2,4-oxadiazol-3-ylmethoxy]phenyl]-5-[H-tetrazol-5yl]-1H-benzimidazole (34) (alternate route to example 5)

Compound 37 from the preceding experiment was added to 2.0 mL of methylene chloride:TFA:triisopropylsilane (6:2:0.5). The mixture was shaken at rt for 20 min and was filtered. The resin was washed with methylene chloride (2×2 mL). The washings and filtrate were combined and concentrated on a rotary evaporator to afford 34 as a TFA salt (56 mg, 70% yield). ESI MS m/e 549 (M+1). The product was identical to that described in Example 5.

INTERMEDIATE 39

3-[[4-[1-Cyclohexyl-5-[2-(triphenylmethyl)-2H-tetrazol-5-yl]-1H-benzimidazole-2-yl]phenoxymethyl]-4-(5-acetyl-2-thienyl) benzoic acid methyl ester (39)

A mixture of compound 23 (500 mg, 0.60 mmol) and 2-acetyl-5-thiopheneboronic acid (112 mg, 0.66 mmol) in dimethoxyethane (4 mL) was degassed for 15 min with a gentle stream of nitrogen. Tetrakis(triphenylphosphine)palladium (0) (69 mg, 0.06 mmol) and a degassed solution of potassium phosphate (1 g, 4.7 mmol) in water (0.7 mL) were added. The mixture was stirred for 18 h at 80° C. and concentrated. The residue was extracted with ethyl acetate and filtered. The filtrate was reconcentrated and the residue chromatographed on silicic acid (14 g) using the flash technique and eluting with mixtures of ethyl acetate and hexanes (1:4) to afford 39 (173 mg, 33% yield). ESI MS m/e 876 (M+1)

INTERMEDIATE 40

3-[[4-[1-Cyclohexyl-5-[2-(triphenylmethyl)-2H-tetrazol-5-yl]-1H-benzimidazole-2-yl]phenoxymethyl]-4-(5-acetyl-2-thienyl) benzoic acid (40)

A mixture of compound 39 (169 mg, 0.19 mmol) and lithium hydroxide (23 mg, 0.97 mmol) in water (1 mL), ethanol (2 mL), and THF (2 mL) was stirred under reflux for 3 h and cooled and acidified with dilute hydrochloric acid to precipitate 40 which was dried in vacuo to afford 147 mg (90% yield). ESI MS m/e 862 (M+1)

EXAMPLE 6 tert-Butyl N-[4-(5-acetylthien-2-yl)-3-({4-[1-cyclohexyl-5-(1H-tetrazol-5-yl]-1H-benzimidazol-2-yl]phenoxy}methyl)benzoyl]glycinate (42)

Compound 40 (23.2 mg, 0.027 mmol), tert-butyl glycinate (4.4 mg, 0.34 mmol), N,N-diisopropylethylamine (14 mg, 0.11 mmol), and 2-[1H-benzotriazol-1-yl]-1,1,3,3,-tetramethyluronium tetrafluoroborate (TBTU, 11 mg, 0.034 mmol) were added to DMF (0.6 mL) in a fritted vial. The vial was sealed and shaken at rt for 2 h in a Bodan MiniB1 II reactor Block™. The mixture was filtered and the residual solid was washed with methanol (3×0.3 mL). The combined filtrate and washings were concentrated to dryness using a Speed Vac® Plus. The residue was dissolved in methanol and the solution purified by preparative HPLC to afford 42 as a TFA salt (6.0 mg, 26% yield). ESI MS m/e 732 (M+1).

EXAMPLE 7

N-[4-(5-Acetylthien-2-yl)-3-({4-[1-cyclohexyl-5-(1H-tetrazol-5-yl]-1H-benzimidazol-2-yl]phenoxy}methyl)benzoyl]glycine (43)

TFA:methylene chloride (0.6 mL of 1:1) was added to compound 42 (3.0 mg, 0.0035 mmol) in a vial contained in a Bodan MiniB1 II reactor Block™ The block was shaken for 30 min and the contents of the vial filtered. The vial was washed with methylene chloride (2×0.4 mL) and the combined filtrate and washings concentrated to dryness using a Speed Vac® Plus. The residue was dissolved in methanol and the solution purified by preparative HPLC to afford 43 as a TFA salt (1.9 mg, 70% yield). ESI MS m/e 676 (M+1).

INTERMEDIATE 45

Methyl 4-(cyclohexylamino)-3-nitrobenzoate (45)

A solution of methyl 4-chloro-3-nitrobenzoate (5.00 g, 23.2 mmol), cylohexylamine (3.98 mL, 34.8 mmol), and triethylamine (4.8 ML, 35 mmol) in acetonitrile (75 mL) was reluxed for 22 h under an argon atmosphere. The reaction mixture was concentrated to a volume of ~20 mL and the precipitated solid was filtered. The filtrate was diluted with ethyl acetate and was washed with 1M citric acid (1×) followed by saturated $NaHCO_3$ (1×). The organic layer was dried ($MgSO_4$) and concentrated on a rotary evaporator. The residue was purified by column chromatography (silica gel, 50–70% dichloromethane/hexanes (v/v)) to give compound 45 as a yellow solid (6.32 g, 98%). ESI-MS m/e 279.2 (M+1).

INTERMEDIATE 46

Methyl 3-amino-4-(cyclohexylamino)benzoate (46)

A solution of compound 45 (2.03 g, 7.29 mmol) in a mixture of methanol (25 mL) and ethyl acetate (25 mL) was hydrogenated over 10% palladium on carbon (0.20 g) at 25 psi for 15 h. The reaction mixture was filtered and concentrated to afford compound 46 as a crude grey-brown oil (1.99 g, 100%). ESI-MS m/e 249.3 (M+1).

INTERMEDIATE 47

Methyl 3-{[4-(benzyloxy)benzoyl]amino}-4-(cyclohexylamino)benzoate (47)

A solution of 4-benzyloxybenzoic acid (2.50 g, 11.0 mmol) and thionyl chloride (1.2 mL, 16 mmol) in benzene (35 mL) was refluxed for 3 h under an argon atmosphere. The reaction mixture was cooled to rt and concentrated on a rotary evaporator. The residue was coevaporated with benzene (2×) to afford the acid chloride as a white solid. A solution of the acid chloride (0.333 g, 1.35 mmol) and compound 46 (0.275 g, 1.11 mmol) in dichloromethane (3 mL) was treated with triethylamine (0.22 mL) at rt. After 30 min, the reaction mixture was diluted with ethyl acetate and washed with 1 M $KHSO_4$ (1×), saturated $NaHCO_3$ (1×), and brine (1×). The organic layer was dried ($MgSO_4$) and concentrated on a rotary evaporator to afford compound 47 as a burgundy foam (0.558 g, 100%). ESI-MS m/e 459.3 (M+1).

INTERMEDIATE 48

Methyl 2-[4-(benzyloxy)phenyl]-1-cyclohexyl-1H-benzimidazole-5-carboxylate (48)

A solution of compound 47 (0.558 g, 1.11 mmol) in acetic acid (3 mL) was refluxed for 1 h and then stirred at 100° C. for 15 h. The reaction mixture was cooled to rt and concentrated on a rotary evaporator. The residue was coevaporated with toluene (1×) and then purified by column chromatography (silica gel, 8% acetone/toluene (v/v)) to give compound 48 as a white solid (0.234 g, 53%). ESI-MS m/e 441.3 (M+1).

INTERMEDIATE 49

2-[4-(Benzyloxy)phenyl]-1-cyclohexyl-1H-benzimidazole-5-carboxylic acid (49)

A solution of compound 48 (0.514 g, 1.17 mmol) in tetrahydrofuran (5 mL) and ethanol (5 mL) was treated with 4 M NaOH (5 mL). The reaction mixture was refluxed for 1 h, cooled to rt, and concentrated on a rotary evaporator. The residue was dissolved in a small amount of water and made acidic with concentrated hydrochloric acid. The solid precipitate was filtered, washed with water, and dried to afford 49 as a white solid (0.52 g, 100%). ESI-MS m/e 427.3 (M+1).

EXAMPLE 8

({2-[4-(Benzyloxy)phenyl]-1-cyclohexyl-1H-benzimidazol-5-yl}carbonyl)benzenesulfonamide (55)

A suspension of compound 49 (0.060 g, 0.14 mmol) and thionyl chloride (0.051 mL) in benzene (2 mL) was refluxed for 2 h under an argon atmosphere. The reaction mixture was cooled to rt and concentrated on a rotary evaporator. The residue was coevaporated with benzene (2×) to afford the acid chloride as a white solid (0.062 g, 100%). Sodium hydride (0.0101 g, 0.252 mmol, 60% dispersion in oil was added to a solution of phenylsulfonamide (0.0425 g, 0.270 mmol) in dimethylformamide (1 mL) at rt under an argon atmosphere. After 1 h, dichloromethane was added (1 mL), followed by the acid chloride of 49 at 0° C. The reaction was warmed to rt. After 1 h, the reaction was diluted with dichloromethane and quenched with 1 N hydrochloric acid. The aqueous layer was washed with dichloromethane (3×). The combined organic layers were dried ($MgSO_4$) and concentrated on a rotary evaporator. The residue was purified by column chromatography (silica gel, 25% acetone/toluene (v/v)). This material was further purified by reverse phase HPLC (C18 column, water/acetonitrile gradient containing 0.05% trifluoroacetic acid) to afford 55 as a white solid (0.0219 g, 54%). $^1$H NMR ($CDCl_3$) δ 8.71 (d, 1H, J=1.1 Hz), 8.05 (m, 3H), 7.82 (d, 1H, J=8.8 Hz), 7.69 (d, 2H, J=9.1 Hz), 7.58 (m, 1H), 7.51–7.36 (m, 7H), 7.21 (d, 2H, 8.8 Hz), 5.16 (s, 2H), 4.52 (m, 1H), 2.32 (br m, 2H), 2.01 (br m, 4H), 1.80 (br m, 1H), 1.35 (br m, 3H); ESI-MS m/e 566.4 (M+1); HPLC purity (ELSD)>95%.

EXAMPLE 9

N-({2-[4-(Benzyloxy)phenyl]-1-cyclohexyl-1H-benzimidazol-5-yl}carbonyl)methanesulfonamide Methanesulfonamide (0.0188 g, 0.198 mmol), sodium hydride, and the acid chloride of 49 (0.0083 g, 0.019 mmol)

were reacted in dimethylformamide and dichloromethane according to the procedure described for example 8. The crude material was purified by reverse phase HPLC (C18 column, water/acetonitrile gradient containing 0.05% trifluoroacetic acid) to afford the product as a white solid (0.0055 g, 52%). $^1$H NMR (CDCl$_3$) δ 8.68 (s, 1H), 8.17 (d, 1H, J=8.8 Hz), 7.91 (d, 1H, J=8.8 Hz), 7.69 (d, 2H, J=8.5 Hz), 7.48–7.37 (m, 5H), 7.24 (d, 2H, J=8.7 Hz), 5.18 (s, 2H), 4.57 (m, 1H), 3.34 (s, 3H), 2.34 (br m, 2H), 2.06 (br m, 4H), 1.85 (br m, 1H), 1.39 (br m, 3H); ESI-MS m/e 504.3 (M+1); HPLC purity (ELSD)>95%.

EXAMPLE 10

3-{2-[4-(Benzyloxy)phenyl]-1-cyclohexyl-1H-benzimidazol-5-yl}-1,2,4-oxadiazol-5(4H)-one (Two steps)

2-[4-(Benzyloxy)phenyl]-1-cyclohexyl-N'-hydroxy-1H-benzimidazole-5-carboximidamide (Step 1) Triethylamine (0.040 mL, 2.9 mmol) was added to hydroxylamine hydrochloride (0.212 g, 3.05 mmol) in dimethyl sulfoxide (1.5 mL). The insoluble material was removed by filtration and washed with tetrahydrofuran (5 mL). The filtrate was concentrated on a rotary evaporator. To the resulting solution of hydroxylamine in dimethylsulfoxide was added nitrile 12 (0.250 g, 0.61 mmol). The solution was heated to 75° C. for 16 h. The resulting suspension was diluted with water, extracted with ethyl acetate, and washed with 1N hydrochloric acid. The aqueous layer was made basic with 1N sodium hydroxide and extracted with ethyl acetate (2×). This ethyl acetate solution was washed with water (1×) and brine (1×), dried (MgSO$_4$) and concentrated on a rotary evaporator to afford the product as a white solid (0.197 g, 96%). ESI-MS m/e 441.3 (M+1).

3-{2-[4-(Benzyloxy)phenyl]-1-cyclohexyl-1H-benzimidazol-5-yl}-1,2,4-oxadiazol-5(4H)-one (Step 2) Methylchloroformate (0.020 mL, 0.26 mmol) was added dropwise to a suspension of the preceding product (0.088 g, 0.2 mmol) and pyridine (0.020 mL, 0.25 mmol) in dimethylformamide (1 mL) at 0° C. The resulting clear solution was stirred overnight at rt. Water was added to the mixture and a precipitate was collected by filtration. The solid was refluxed in xylene for 3 hours, during which time the reaction became a clear solution, then formed a new precipitate. This material was filtered and washed with hexane, to afford the product as a white solid (0.038 g, 41%). $^1$H NMR (CD$_3$OD) δ 8.06 (s, 1H), 7.91 (d, 1H, J=8.8 Hz), 7.78 (d, 1H, J=8.4 Hz), 7.59 (d, 2H, J=8.8 Hz), 7.49 (d, 2H, J=7.7 Hz) 7.44–7.32 (m, 3H), 7.22 (d, 2H, J=8.8 Hz), 5.21 (s, 2H), 4.41 (m, 1H), 2.45–2.25 (m, 2H), 1.98 (m, 4H), 1.78 (m, 1H), 1.39 (m, 3H); ESI-MS m/e 467.3 (M+1); HPLC purity (ELSD) 91%.

EXAMPLE 11

2-[4-(Benzyloxy)phenyl]-1-cyclohexyl-5-(2-oxido-3H-1,2,3,5-oxathiadiazol-4-yl)-1H-benzimidazole Thionyl chloride (0.010 mL, 0.14 mmol) was added dropwise to a suspension of 2-[4-(Benzyloxy)phenyl]-1-cyclohexyl-N'-hydroxy-1H-benzimidazole-5-carboximidamide (0.025 g, 0.057 mmol, see above for preparation) and pyridine (0.020 mL, 0.25 mmol) in tetrahydrofuran (2 mL) at 0° C. The resulting solution was stirred for 3 h, and then concentrated on a rotary evaporator. As starting material remained, the residue was resubjected to the reaction conditions (0.020 mL thionyl chloride and 0.040 mL pyridine). The residue was purified by reverse phase HPLC (C18 column, water/acetonitrile gradient containing 0.05% trifluoroacetic acid) to afford the product as a yellow solid (0.011 g, 32%). $^1$H NMR (CD$_3$OD) δ 8.32 (d, 1H, J=8.8 Hz), 8.25 (s, 1H), 8.04 (d, 1H, J=8.8 Hz), 7.77 (d, 2H, J=9.1 Hz), 7.49 (d, 2H, J=6.6 Hz) 7.43–7.35 (m, 5H), 5.27 (s, 2H), 4.55 (m, 1H), 2.45 (m, 2H), 2.15 (m, 2H), 2.00 (m, 2H), 1.80 (m, 1H), 1.44 (m, 3H); ESI-MS m/e 487.3 (M+1); HPLC purity (ELSD)>95%.

INTERMEDIATE 56

6-Chloro-5-nitronicotinic acid (56)

A suspension of 6-hydroxy-5-nitronicotinic acid (8 g, 43.5 mmol) (prepared by literature nitration of 6-hydroxynicotinic acid) in phosphorus oxychloride (24.3 mL, 261.0 mmol) was heated to reflux (105° C.) for 3 h under a nitrogen atmosphere. At the end of this time period all of the solids had dissolved. The reaction was cooled to rt and poured over 500 mL crushed ice, and stirring was continued for 30 minutes until all of the ice had melted. The aqueous mixture was extracted with a 1:2 mixture of THF in diethyl ether (3×150 mL). The pooled organic extracts were washed with brine (1×), dried (MgSO$_4$), and concentrated on a rotary evaporator to afford intermediate 56 as a light brown solid (8.37 g, 95%). ESI-MS m/e 405.3 (2M-1).

INTERMEDIATE 57

6-(Cyclohexylamino)-5-nitronicotinic acid (57)

To a solution of intermediate 56 (10.1 g, 49.9 mmol) and triethylamine (14.6 mL, 125.0 mmol) in acetonitrile (130 mL) and DMSO (25 mL) was added cyclohexylamine (13.7 mL, 100 mmol). The reaction mixture was heated to reflux (90° C.) under a nitrogen atmosphere for 20 h. The reaction mixture was cooled to rt and concentrated on a rotary evaporator and the residue was dissolved in 800 mL 1N sodium hydroxide solution. This solution was washed with dichloromethane (3×75 mL) and then made acidic (pH=5) with concentrated hydrochloric acid. The precipitated product was collected by vacuum filtration and washed sparingly with cold water to afford the HCl salt of intermediate 57 as a yellow solid (9.8 g, 65%). ESI-MS m/e 266.2 (M+1).

INTERMEDIATE 58

Methyl 6-(cyclohexylamino)-5-nitronicotinate (58)

To a solution of intermediate 57 (9.7 g, 32.2 mmol) in methanol (400 mL) was added chlorotrimethylsilane (3 mL) to achieve pH=2. The reaction mixture was heated at strong reflux for 72 h, during which time the pH was monitored and more chlorotrimethylsilane added as necessary to maintain an acidic solution. The reaction mixture was allowed to cool and was then concentrated on a rotary evaporator. The residue was purified by column chromatography (silica gel, 7:2:1 hexanes/dichloromethane/methanol) to afford the crude ester as a yellow solid (9.0 g, 89%). ESI-MS m/e 280.1 (M+1).

A solution of the ester (9.0 g, 32.2 mmol) and 10% palladium on carbon (450 mg) in 1.3:1 ethyl acetate/methanol (220 mL) was placed on a PARR hydrogenation shaker under a hydrogen atmosphere at 55 p.s.i. for 2.5 h. After hydrogen uptake had ceased, the solution was filtered to remove the Pd/C and then concentrated on a rotary evaporator. The oily residue was dissolved in acetonitrile (10 mL) and a small amount of water (1×2 mL) was added to cause a slight cloudiness. This solution was then frozen solid in a dry ice/acetone bath and placed on the lyophilizer overnight to afford intermediate 58 as a yellow solid (8.04 g, 100%). ESI-MS m/e 250.1 (M+1).

INTERMEDIATE 59

Methyl 3-cyclohexyl-2-(4-hydroxyphenyl)-3H-imidazo[4,5-b]pyridine-6-carboxylate (59)

A solution of intermediate 58 (5.0 g, 20.0 mmol) and ethyl 4-hydroxybenzimidate hydrochloride (6.0 g, 30.0 mmol) in methanol (67 mL) was heated at reflux for 22 h. The reaction mixture was then cooled to rt and the precipitated solid was collected by vacuum filtration and washed sparingly with cold methanol to afford intermediate 59 as a white solid (6.13 g, 88%). ESI-MS m/e 352.2 (M+1).

INTERMEDIATE 60

3-Cyclohexyl-2-(4-hydroxy-phenyl)-3H-imidazo[4,5-b]pyridine-6-carboxylic acid (2-cyano-ethyl)-amide (60)

A solution of Intermediate 59 (1.5 g, 4.3 mmol) in tetrahydrofuran (5 mL) and ethanol (5 mL) was treated with 4 M NaOH (5 mL). The reaction mixture was refluxed for 1 h, cooled to rt, and concentrated on a rotary evaporator. The residue was dissolved in a small amount of water and made acidic with concentrated hydrochloric acid. The solid precipitate was filtered, washed, and dried to afford the acid as a white solid (1.4 g, 97%). ESI-MS m/e 338.1 (M+1).

The crude acid (1.4 g, 4.15 mmol), 1-hydroxybenzotriazole (1.27 g, 8.3 mmol), sodium bicarbonate (628 mg, 7.47 mmol), and 2-cyanoethylamine (332 µL, 4.98 mmol) were dissolved in a 5:1 mixture of dimethylformamide/dichloromethane (12 mL). To this solution was added ethyl-3-(3dimethylamino-propyl) carbodiimide (955 mg, 4.98 mmol) at rt, and the resulting reaction mixture was stirred for 18 h at rt under a nitrogen atmosphere. The reaction mixture was concentrated on a rotary evaporator to an approximate volume of 4 mL and then ethyl acetate (75 mL) was added and the solids removed by vacuum filtration. The filtrate was washed with 0.1 N HCl (1×), saturated NaHCO3 (1×), and brine (1×). The organic phase was dried (Na$_2$SO$_4$) and concentrated to afford the HCl salt of intermediate 60 as a white solid (1.4 g, 80%). ESI-MS m/e 390.1 (M+1).

INTERMEDIATE 61

2-[4-(tert-Butyl-dimethyl-silanyloxy)-phenyl]-3-cyclohexyl-3H-imidazo[4,5-b]pyridine-6-carboxylic acid (2-cyano-ethyl)-amide (61)

To a solution of intermediate 60 (1.5 g, 3.85 mmol) in dimethylformamide (5 mL) was added imidazole (0.917 g, 13.5 mmol) and tert-butyldimethylsilyl chloride (0.870 g, 5.77 mmol). The reaction mixture was stirred at 35° C. for 20 h, and then ethyl acetate (100 mL) was added. The resulting organic phase was washed with water (4×20 mL) and brine (1×) and then dried (Na$_2$SO$_4$). After concentrating on a rotary evaporator the resulting residue was purified by column chromatography (silica gel, 1:1 hexanes/ethyl acetate-3:7 hexanes/ethyl acetate) to afford intermediate 61 as a white solid (1.6 g, 83%). ESI-MS m/e 504.0 (M+1).

INTERMEDIATE 62

3-(5-{2-[4-(tert-Butyl-dimethyl-silanyloxy)-phenyl]-3-cyclohexyl-3H-imidazo[4,5-b]pyridin-6-yl}-tetrazol-1-yl)-propionitrile (62)

A solution of intermediate 61 (250 mg, 0.5 mmol), sodium azide (33 mg, 0.5 mmol), and 2,6-lutidine (116 µL, 1.0 mmol) in dichloromethane (3 mL) was cooled to 0° C. and trifluoromethanesulfonic anhydride (84 µL, 0.5 mmol) from a freshly opened ampule was added under a nitrogen atmosphere. The reaction mixture was allowed to warm up slowly to rt over 2 h and stirring continued for 20 h at which point dichloromethane was added (25 mL). The resulting organic phase was washed with saturated NaHCO$_3$ (1×20 mL), dried (Na$_2$SO$_4$), and concentrated on a rotary evaporator. The foamy residue was purified by reverse phase HPLC (C18 column, water/acetonitrile gradient containing 0.05% trifluoroacetic acid) to afford intermediate 62 as a white solid (48 mg, 18%). ESI-MS m/e 529.1 (M+1).

INTERMEDIATE 63

3-{5-[3-Cyclohexyl-2-(4-hydroxy-phenyl)-3H-imidazo[4,5-b]pyridin-6-yl]-tetrazol-1-yl}-propionitrile (63)

A solution of intermediate 62 (78 mg, 0.15 mmol) in glacial acetic acid (3 mL), tetrahydrofuran (1 mL), and water (1 mL) was heated to 100° C. for 3 h under a nitrogen atmosphere. Ethyl acetate (40 mL) was added and the organic phase washed with water (2×20 mL), NaHCO$_3$ (2×20 mL), and brine (1×). The organic phase was dried (Na$_2$SO$_4$) and concentrated on a rotary evaporator to afford intermediate 63 as a white solid (54 mg, 89%). ESI-MS m/e 415.1 (M+1).

INTERMEDIATE 63a 2-(Bromomethyl)-4'-cyano-N-methyl-1,1'-biphenyl-4-carboxamide (3 Steps)

(Step 1) A solution of tert butyl 4-bromo-3-methylbenzoate (3.3 g, 12.2 mmol) was reacted with 4-cyanophenylboronic acid (2.15 g, 14.6 mmol) according to the procedure described for compound 14. The crude product was purified by column chromatography (silica gel, 3:2 hexanes/methylene dichloride) to afford tert-butyl 4'-cyano-2-methyl-1,1'-biphenyl-4-carboxylate as a white solid (3.0 g, 84% yield). ESI-MS m/e 294.1 (M+1).

(Step 2) To a solution of the preceding ester (3.0 g, 10.2 mmol) in methylene chloride (75 mL) at 0° C. was added TFA (75 mL) dropwise over 10 min. The ice bath was removed and stirring continued for 1 h at rt. The mixture was concentrated on a rotary evaporator and then diluted with toluene and reconcentrated to afford 4'-cyano-2-methyl-1,1'-biphenyl-4-carboxylic acid. ESI-MS m/e 228.1 (M+1).

(Step 3) To a solution of the preceding acid (760 mg, 3.2 mmol), 2M methylamine in tetrahydrofuran (3.1 mL, 6.2 mmol), and diisopropylethylamine (1.71 mL, 9.6 mmol) in dimethylformamide (15 mL) was added benzotriazol-1-yloxytris(dimethylamino)phosphonium hexafluorophosphate (1.72 g, 3.89 mmol) under a nitrogen atmosphere. The reaction mixture was stirred at rt for 1 h, at which point the reaction mixture was diluted with dichloromethane 50 mL) and washed with water (2×15 mL), saturated NaHCO3 (2×15 mL), and brine (1×). The organic phase was then dried (Na$_2$SO$_4$) and concentrated on a rotary evaporator. The crude material was purified by column chromatography (silica gel, 1:1 dichloromethane/hexane to 100% dichloromethane) to obtain the amide intermediate, 2-methyl-4'-cyano-N-methyl-1,1'-biphenyl-4-carboxamide, which was dissolved in dichloromethane (15 mL). N-bromosuccinimide (1.14 g, 6.4 mmol) was added. The reaction mixture was irradiated with an ultraviolet light for 4 h under reflux and under a nitrogen atmosphere. The reaction mixture was concentrated with a rotary evaporator and the residue purified by reverse phase HPLC (C18 column, water/acetonitrile gradient containing 0.05% trifluoroacetic acid) to afford the titled compound as a white solid (210 mg, 20% yield). ESI-MS m/e 329.1 (M+1).

EXAMPLE 12

4'-Cyano-2-{4-[3-cyclohexyl-6-(1H-tetrazol-5-yl)-3H-imidazo[4,5-b]pyridin-2-yl]-phenoxymethyl}-biphenyl-4-carboxylic acid methylamide (64)

Intermediate 63 (50 mg, 0.12 mmol) in dimethylformamide was reacted with 2-(bromomethyl)-4'-cyano-N-methyl-1,1'-biphenyl-4-carboxamide (63a) (40 mg, 0.12 mmol), cesium carbonate (20 mg, 0.06 mmol) and the resulting suspension stirred under a nitrogen atmosphere at rt for 3h at which point ethyl acetate (30 mL) was added. The organic phase was washed with water (2×25 mL) and brine (1×), dried ($Na_2SO_4$), and concentrated on a rotary evaporator. The resulting residue was dissolved in 10% methanolic sodium hydroxide (5 mL) and water (2 mL) was added. The resulting solution was stirred at rt under a nitrogen atmosphere for 30 minutes at which point 10% hydrochloric acid was added until pH=2. This solution was extracted with ethyl acetate, dried ($Na_2SO_4$), and concentrated on a rotary evaporator and the residue purified by reverse phase HPLC (C18 column, water/acetonitrile gradient containing 0.05% trifluoroacetic acid) to afford the product as a white solid (6 mg, 7%). $^1$H NMR ($CD_3OD$) δ 9.16 (s, 1H), 8.7 (br s, 1H), 8.15 (d, 1H, J=1.46), 7.94 (dd, 1H, J=8.06, 1.83), 7.80 (d, 2H, J=8.42), 7.71 (br m, 2H), 7.65 (d, 2H, J=8.06), 7.49 (d, 1H, J=8.06), 7.17 (d, 2H, 6.59), 5.14 (s, 1H), 4.46 (br m, 1H), 2.96 (s, 3H), 2.83 (br m, 2H), 1.96 (br m, 4H), 1.75 (br m, 1H), 1.39 (br m, 3H); ESI-MS m/e 610.24 (M+H); HPLC purity (ELSD)>95%.

Using these methods examples 13 and 14 were prepared.

EXAMPLE 13

4'-Chloro-2-{4-[3-cyclohexyl-6-(1H-tetrazol-5-yl)-3H-imidazo[4,5-b]pyridin-2-yl]-phenoxymethyl}-biphenyl-4-carboxylic acid methylamide White solid (6 mg, 15%). $^1$H NMR ($CD_3OD$) δ 9.17 (s, 1H), 8.67 (s, 1H), 8.13 (s, 1H), 7.90 (dd, 1H, J=8.06, 1.46 Hz), 7.69 (d, 2H, J=8.06), 7.48 (s, 1H), 7.45 (m, 4H), 7.18 (d, 2H, J=8.06), 5.13 (s, 2H), 4.46 (m, 1H), 2.96 (s, 3H), 2.83 (br m, 2H), 1.98 (br m, 4H), 1.75 (br m, 1H), 1.4 (br m, 3H); ESI-MS m/e 619.2 (M+1); HPLC purity (ELSD)>95%.

EXAMPLE 14

N-[(2-{4-[(4'-Chloro-4-methoxy-1,1'-biphenyl-2-yl)methoxy]phenyl}-3-cyclohexyl-3H-imidazo[4,5-b]pyridin-6-yl)carbonyl]methanesulfonamide White solid (11 mg, 14%). $^1$H NMR ($CDCl_3$) δ 8.84 (d, 1H, J=1.8 Hz), 8.48 (d, 1H, J=1.9 Hz), 7.61 (d, 2H, J=8.8 Hz), 7.42 (m, 4H), 7.34 (d, 1H, 9.2), 7.29 (d, 1H, J=4.4 Hz), 7.04 (m, 3H), 5.03 (s, 2H), 4.36 (br m, 1H), 3.84 (s, 3H), 3.29 (s, 3H), 2.69 (br m, 2H), 1.94 (br m, 4H), 1.70 (br m, 1H), 1.32 (br m, 3H); ESI-MS m/e 645.1 (M+1); HPLC purity (ELSD)>95%.

INTERMEDIATE 66

4-(cyclohexylamino)-3-nitrobenzenesulfonamide (66)

A solution of 4-chloro-3-nitro-benzene sulfonamide (5.49 g, 23.2 mmol), cyclohexylamine (4.00 mL, 35.0 mmol), and triethylamine (5.0 mL, 35 mmol) in acetonitrile (75 mL) was refluxed overnight under nitrogen atmosphere. The reaction mixture was concentrated almost to dryness. The residue was diluted in ethyl acetate and washed with 1N hydrochloric acid (1×) and saturated $NaHCO_3$ (1×). The organic layer was dried ($MgSO_4$) and concentrated on a rotary evaporator. The residue was filtered and washed with hexane to give the product as a yellow solid (6.34 g, 91%). ESI-MS m/e 300.1 (M+1).

INTERMEDIATE 67

3-amino-4-(cyclohexylamino)benzenesulfonamide (67)

A solution of intermediate 66 (2.56 g, 8.55 mmol) in a mixture of methanol (50 mL) and ethyl acetate (50 mL) was hydrogenated over 10% palladium on carbon (0.14 g) at 50 psi for 2.5 h. The reaction mixture was filtered and concentrated to afford the product as a crude purple-brown foam (2.45 g, 100%). ESI-MS m/e 270.1 (M+1).

INTERMEDIATE 68

1-cyclohexyl-2-(4-(hydroxy)phenyl-1H-benzimidazole-5-sulfonamide (68)

A solution of ethyl-4 hydroxy benzimidate hydrochloride (1.01 g, 5.0 mmol) and intermediate 67 (1.5 g, 5.0 mmol) in methanol (10 ML) was refluxed overnight under a nitrogen atmosphere. The reaction mixture was cooled to rt and t solid was filtered and washed with methanol to afford the pinkish brown solid (1.26 g, 68%). ESI-MS m/e 372.1 (M+1).

INTERMEDIATE 69

2-[4-(Benzyloxy)phenyl]-1-cyclohexyl-1H-benzimidazole-5-sulfonamide (69)

A suspension of intermediate 68 (0.556 g, 1.50 mmol) in N,N-dimethylformamide (4 mL) and cesium carbonate (0.487 g, 1.49 mmol) was heated at 40° C. until almost clear. Benzyl bromide (0.201 ml, 1.65 mmol) was added drop wise. The reaction mixture was stirred at rt overnight. The mixture was concentrated on a rotary evaporator. The residue was washed with water and filtered to give a white solid precipitate which was filtered, and then purified by column chromatography (silica gel, 50% to 100% hexane/ethyl acetate (v/v)) to give the product as a white solid (0.300 g, 44%). ESI-MS m/e 462.1 (M+1).

EXAMPLE 15

N-acetyl-2-[4-(Benzyloxy)phenyl]-1-cyclohexyl-1H-benzimidazol-5-sulfonamide

A solution of intermediate 69 (0.023 g, 0.05 mmol) in N,N-dimethylformamide (0.200 mL) and lithium bis (trimethylsilyl)amide (1.0 M solution in tetrahydrofuran) (0.050 ml, 0.05 mmol) was cooled to 0° C. Acetyl chloride (0.005 ml, 0.06 mmol) was added. The reaction mixture was stirred at rt for 1.5 h. At this time, more lithium bis (trimethylsilyl)amide solution (0.050 ml, 0.05 mmol) and acetyl chloride (0.010 ml, 0.014 mmol) were added. The reaction was stirred at rt overnight and concentrated. The crude material was purified by reverse phase HPLC (C18 column, water/acetonitrile gradient containing 0.05% trifluoroacetic acid) to afford the product as a white solid (0.006 g, 18%). $^1$H NMR ($CDCl_3$) δ 8.52 (br s, 1H), 8.15 (br s, 1H), 7.84 (br m, 1H), 7.61 (br m, 2H), 7.47–7.29 (br m, 5H), 7.22

(br m, 2H), 5.18 (s, 2H), 4.46 (m, 1H), 2.30 (br m, 4H), 2.01 (br m, 2H), 1.82 (br m, 1H), 1.37 (br m, 3H); ESI-MS m/e 504.1 (M+1); HPLC purity (ELSD) 100%.

EXAMPLE 16

N-Benzoyl-2-[4-(benzyloxy)phenyl]-1-cyclohexyl-1H-benzimidazol-5-sulfonamide

Intermediate 69 (0.023 g, 0.05 mmol) and benzoyl chloride (0.005 ml, 0.06 mmol) were used to prepare the titled compound (0.006 g, 18%) by the same method as in example 15. $^1$H NMR (CDCl$_3$) δ 8.59 (s, 1H), 8.26 (d, 1H, J=8.8 Hz), 7.84 (m, 3H), 7.59 (d, 211, J=8.8 Hz), 7.56–7.37 (m, 8H), 7.18 (d, 2H, J=8.4 Hz), 5.17 (s, 2H), 4.42 (m, 1H), 2.33 (br m, 4H), 1.99 (br m, 2H), 1.81 (br m, 1H), 1.36 (br m, 3H); ESI-MS m/e 566.1 (M+1); HPLC purity (ELSD) 100%.

EXAMPLE 17

4-[2-(4-Benzyloxyphenyl)-1-cyclohexyl-1H-benzoimidazole-5-sulfonylaminocarbonyl]-benzoic acid methyl ester A solution of intermediate 69 (0.046 g, 0.1 mmol) in dichloromethane (0.500 mL) was cooled to 0° C. and lithium bis(trimethylsilyl)amide (1.0 M solution in tetrahydrofuran) (0.12 ml, 0.12 mmol) was added and stirred for 5 min. P-phthalic acid mono methyl ester chloride (0.021 g, 0.11 mmol) was added. The reaction mixture was stirred at rt for 4 hrs. The crude material was concentrated and purified by reverse phase HPLC (C18 column, water/acetonitrile gradient containing 0.05% trifluoroacetic acid) to afford the titled compound (0.024 g, 38%). $^1$H NMR (CDCl$_3$) δ 8.45 (s, 1H), 8.17 (d, 1H, J=8.8 Hz), 8.07 (d, 2H, J=8.4 Hz), 7.91 (d, 2H, J=8.8 Hz), 7.85 (d, 1H, J=8.8 Hz), 7.56 (d, 2H, J=8.8 Hz), 7.50–7.37 (m, 5H), 7.18 (d, 2H, J=8.8 Hz), 5.18 (s, 2H), 4.41 (m, 1H), 4.00 (bs, 3H), 2.31 (br m, 2H), 2.02 (br m, 4H), 1.80 (br m, 1H), 1.36 (br m, 3H); ESI-MS m/e 624.2(M+1); HPLC purity (UV) 99%.

EXAMPLE 18

4-[2-(4-Benzyloxyphenyl)-1-cyclohexyl-1H-benzoimidazole-5-sulfonylaminocarbonyl]-benzoic acid A solution of the preceding ester (0.020 g, 0.03 mmol) in ethanol (1.0 mL), tetrahydrofuran (1.0 mL) and 4N NaOH aq. solution (0.5 mL), was refluxed for 30 min. The reaction mixture was concentrated and treated with 4N HCl aq. Solution until acidic. The solid was filtered and dried to afford the product (0.014 g, 72%). $^1$H NMR (CDCl$_3$) δ 8.46 (s, 1H), 8.2 (d, 1H, J=8.8 Hz), 8.08 (d, 2H, J=8.4 Hz), 7.90 (d, 2H, J=8.4 Hz), 7.85 (d, 1H, J=8.8 Hz), 7.56 (d, 2H, J=8.8 Hz), 7.47–7.41 (m, 5H), 7.17 (d, 2H, J=8.8 Hz), 5.18 (s, 2H), 4.40 (m, 1H), 2.31 (br m, 2H), 1.99 (br m, 4H), 1.80 (br m, 1H), 1.36 (br m, 3H); ESI-MS m/e 610.1(M+1); HPLC purity (UV) 94%.

EXAMPLE 19

3-[2-(4-Benzyloxyphenyl)-1-cyclohexyl-1H-benzoimidazole-5-sulfonylamino]-3-oxo-propionic acid methyl ester A solution of intermediate 69 (0.046 g, 0.1 mmol) in dichloromethane (0.700 mL) was cooled to 0° C. Lithium bis(trimethylsilyl)amide (1.0 M solution in tetrahydrofuran) (0.10 ml, 0.10 mmol) was added and the mixture was stirred for 1 hr. Methyl-3-chloro-3-oxo-propionate (0.011 ml, 0.10 mmol was added. The reaction mixture was stirred at rt overnight. The reaction mixture was concentrated and the residue purified by reverse phase HPLC (C18 column, water/acetonitrile gradient containing 0.05% trifluoroacetic acid) to afford the product (0.005 g, 7%). $^1$H NMR (CDCl$_3$) δ 8.60 (s, 1H), 8.16 (d, 1H, J=8.8 Hz), 7.85 (d, 1H, J=8.8 Hz), 7.64 (d, 2H, J=8.8 Hz), 7.50–7.38 (m, 5H), 7.21 (d, 2H, J=8.8 Hz), 5.18 (s, 2H), 4.49 (m, 1H), 3.70 (s, 3H), 3.35 (s, 2H), 2.30 (br m, 2H), 2.02 (br m, 4H), 1.82 (br m, 1H), 1.35 (br m, 3H); ESI-MS m/e 562.18(M+1); HPLC purity (UV) 99%.

EXAMPLE 20

3-[2-(4-Benzyloxy-phenyl)-1-cyclohexyl-1H-benzoimidazole-5-sulfonylamino]-3-oxo-propionic acid The preceding ester was hydrolyzed to yield the product (0.006 g) by the same method as in example 18. $^1$H NMR (CDCl$_3$) δ 8.60 (s, 1H), 8.19 (d, 1H, J=8.5 Hz), 7.97 (d, 1H, J=8.8 Hz), 7.79 (d, 2H, J=7.6 Hz), 7.48–7.37 (m, 5H), 7.26 (m, 2H), 5.18 (s, 2H), 4.57 (m, 1H), 3.35 (bs, 2H), 2.32 (br m, 2H), 2.10 (br m, 2H), 2.02 (br m, 2H), 1.80 (br m, 1H), 1.37 (br m, 3H); ESI-MS m/e 548.04(M+1); HPLC purity (UV)>93%.

EXAMPLE 21

3-[2-(4-Benzyloxy-phenyl)-1-cyclohexyl-1H-benzoimidazole-5-sulfonylamino]-3-oxo-acetic acid methyl ester Intermediate 69 (0.046 g, 0.1 mmol) and methyl-oxalyl chloride (0.010 ml, 0.11 mmol) were used to prepare the titled compound (0.020 g, 30%). $^1$H NMR (CDCl$_3$) δ 8.71 (s, 1H), 8.24 (d, 1H, J=8.8 Hz), 7.91 (d, 1H, J=8.8 Hz), 7.64 (d, 2H, J=8.8 Hz), 7.48–7.38 (m, 5H), 7.22 (d, 2H, J=8.8 Hz), 5.18 (s, 2H), 4.53 (m, 1H), 3.85 (s, 3H), 2.31 (br m, 2H), 2.09 (br m, 4H), 1.84 (br m, 1H), 1.38 (br m, 3H); ESI-MS m/e 548.17(M+1); HPLC purity (UV)>78%.

EXAMPLE 22

[2-(4-Benzyloxy-phenyl)-1-cyclohexyl-1H-benzoimidazole-5-sulfonylamino]-3-oxo-acetic acid The preceding ester (0.012 g, 0.018 mmol) was used to prepare the titled compound (0.005 g, 52%) by the same method as in the previous examples. $^1$H NMR (CDCl$_3$) δ 8.67 (s, 1H), δ 8.47 (bs, 1H), 8.13 (d, 1H, J=8.8 Hz), 7.91 (m, 1H), 7.71 (d, 2H, J=8.8 Hz), 7.49–7.37 (m, 5H), 7.23 (d, 2H, J=8.4 Hz), 5.17 (s, 2H), 4.53 (m, 1H), 2.31 (br m, 2H), 2.06 (br m, 4H), 1.81 (br m, 1H), 1.37 (br m, 3H); ESI-MS m/e 534.1(M+1); HPLC purity (UV) 100%.

Other compounds prepared by these methods are included in the following table.

Master Table.

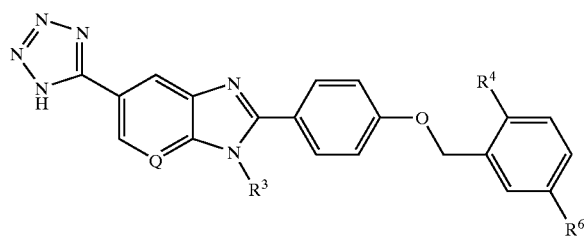

| Ex. No. | Q | R³ | R⁴ | R⁶ | Synthetic method | Retention Time (min) | Purity (AP) | MS (M + 1) |
|---|---|---|---|---|---|---|---|---|
| 23 | CH | cHexyl | 4-ClPh | $CO_2H$ | C | 2.55 | 98 | 605 |
| 24 | CH | cHexyl | 4-FPh | $CO_2H$ | D | 1.82 | 95 | 589 |
| 25 | CH | cHexyl | 4-MeOPh | $CO_2H$ | D | 1.92 | 90 | 601 |
| 26 | CH | cHexyl | 4-MeSPh | $CO_2H$ | D | 2.00 | 90 | 617 |
| 27 | CH | cHexyl | 3,5-di-ClPh | $CO_2H$ | D | 2.09 | 95 | 639 |
| 28 | CH | cHexyl | 1-naphthyl | $CO_2H$ | D | 2.03 | 95 | 621 |
| 29 | CH | cHexyl | 2-biphenyl | $CO_2H$ | D | 1.93 | 95 | 647 |
| 30 | CH | cHexyl | 3-Cl-4-FPh | $CO_2H$ | D | 1.87 | 90 | 623 |
| 31 | CH | cHexyl | 4-CF₃Ph | $CO_2H$ | D | 1.87 | 98 | 639 |
| 32 | CH | cHexyl | 3-AcNHPh | $CO_2H$ | D | 1.61 | 98 | 628 |
| 33 | CH | cHexyl | 3-(OH)Ph | $CO_2H$ | D | 1.78 | 94 | 587 |
| 34 | CH | cHexyl | 4-(CN)Ph | $CO_2H$ | D | 1.78 | 92 | 596 |
| 35 | CH | cHexyl | Ph | $CO_2H$ | D | 1.92 | 95 | 571 |
| 36 | CH | cHexyl | 2-(CHO)Ph | $CO_2H$ | D | 1.79 | 90 | 599 |
| 37 | CH | cHexyl | 4-(CHO)Ph | $CO_2H$ | D | 1.80 | 82 | 599 |
| 38 | CH | cHexyl | 3-($CO_2H$)Ph | $CO_2H$ | D | 1.80 | 90 | 615 |
| 39 | CH | cHexyl | 4-($CO_2H$)Ph | $CO_2H$ | D | 1.78 | 94 | 614 |
| 40 | CH | cHexyl | 4-MeSO₂Ph | $CO_2H$ | D | 1.69 | 92 | 648 |
| 41 | CH | cHexyl | 4-NO₂Ph | $CO_2H$ | D | 1.73 | 98 | 616 |
| 42 | CH | cHexyl | 4-(CH₂OH)Ph | $CO_2H$ | D | 1.50 | 83 | 601 |
| 43 | CH | cHexyl | 3-NH₂-4-MePh | $CO_2H$ | D | 1.40 | 90 | 600 |
| 44 | CH | cHexyl | 3,4-di-MeOPh | $CO_2H$ | D | 1.60 | 95 | 631 |
| 45 | CH | cHexyl | 4-MeCOPh | $CO_2H$ | D | 1.60 | 95 | 613 |
| 46 | CH | cHexyl | 4-(OH)Ph | $CO_2H$ | D | 1.53 | 95 | 587 |
| 47 | CH | cHexyl | 4-(CH=CHCO₂H)Ph | $CO_2H$ | D | 1.60 | 95 | 641 |
| 48 | CH | cHexyl | 4-ClPh | 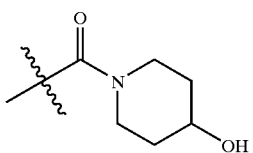 | G | 1.68 | 90 | 688 |
| 49 | CH | cHexyl | 4-CNPh | CONHMe | G |  | 99 | 609 |
| 50 | CH | cHexyl | 4-ClPh | CONHMe | G |  | 99 | 618 |
| 51 | CH | cHexyl | H | 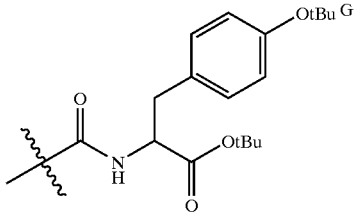 | G | 1.89 | 90 | 770 |
| 52 | CH | cHexyl | 3-(OH)Ph | CONHCH(Me)$CO_2H$ | G | 1.52 | 70 | 658 |
| 53 | CH | cHexyl | 3-(OH)Ph | 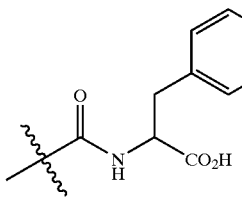 | G | 1.54 | 90 | 750 |

-continued
Master Table.
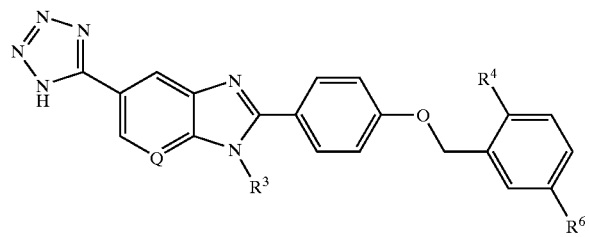
| Ex. No. | Q | R³ | R⁴ | R⁶ | Synthetic method | Retention Time (min) | Purity (AP) | MS (M + 1) |
|---|---|---|---|---|---|---|---|---|
| 54 | CH | cHexyl | 3-(OH)Ph | 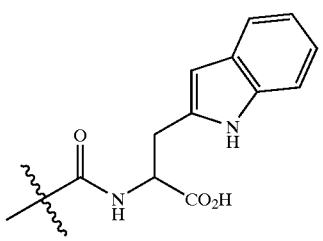 | G | 1.93 | 96 | 773 |
| 55 | CH | cHexyl | 3-(OH)Ph | CONHCH₂CH₂CONH₂ | G | 1.45 | 97 | 657 |
| 56 | CH | cHexyl | 3-Cl-4-FPh | CONHCH(Me)CO₂H | G | 1.63 | 100 | 694 |
| 57 | CH | cHexyl | 3-Cl-4-FPh | 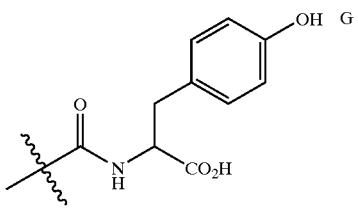 | G | 1.74 | 98 | 786 |
| 58 | CH | cHexyl | 3-Cl-4-FPh | 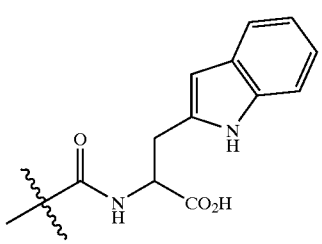 | G | 1.98 | 99 | 809 |
| 59 | CH | cHexyl | 3-Cl-4-FPh | CONHCH₂CH₂CONH₂ | G | 1.58 | 99 | 693 |
| 60 | CH | cHexyl | 3,4-di-MeOPh | CONHCH(Me)CO₂H | G | 1.44 | 90 | 701 |
| 61 | CH | cHexyl | 3,4-di-MeOPh | 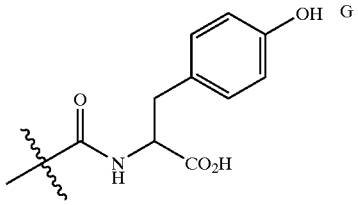 | G | 1.50 | 100 | 794 |

-continued

Master Table.

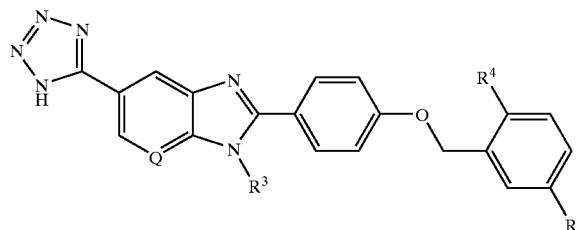

| Ex. No. | Q | R³ | R⁴ | R⁶ | Synthetic method | Retention Time (min) | Purity (AP) | MS (M + 1) |
|---|---|---|---|---|---|---|---|---|
| 62 | CH | cHexyl | 3,4-di-MeOPh | ![tryptophan amide structure] | G | 1.88 | 100 | 816 |
| 63 | CH | cHexyl | 3,4-di-MeOPh | CONHCH₂CH₂CONH₂ | G | 1.54 | 90 | 701 |
| 64 | CH | cHexyl | 3-(OH)Ph | ![N-methylpiperazine amide] | G | 1.46 | 100 | 669 |
| 65 | CH | cHexyl | 3-(OH)Ph | ![morpholine amide] | G | 1.53 | 100 | 656 |
| 66 | CH | cHexyl | 3-(OH)Ph | ![pyrrolidine amide] | G | 1.61 | 100 | 640 |
| 67 | CH | cHexyl | 3-(OH)Ph | CONHCH₂CH₂CH₂OH | G | 1.47 | 100 | 644 |
| 68 | CH | cHexyl | 3-(OH)Ph | CONHMe | G | 1.59 | 100 | 600 |
| 69 | CH | cHexyl | 3-(OH)Ph | ![4-hydroxypiperidine amide] | G | 1.59 | 100 | 670 |
| 70 | CH | cHexyl | 3-(OH)Ph | CON(CH₂CH₂OH)₂ | G | 1.52 | 100 | 674 |
| 71 | CH | cHexyl | 3-(OH)Ph | CONHCH(Me)CO₂tBu | G | 1.72 | 86 | 714 |
| 72 | CH | cHexyl | 3-(OH)Ph | CONHCH₂CO₂tBu | G | 1.79 | 98 | 700 |

-continued
Master Table.
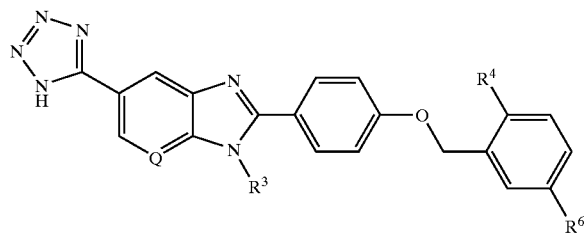
| Ex. No. | Q | R³ | R⁴ | R⁶ | Synthetic method | Retention Time (min) | Purity (AP) | MS (M + 1) |
|---|---|---|---|---|---|---|---|---|
| 73 | CH | cHexyl | 3-(OH)Ph | 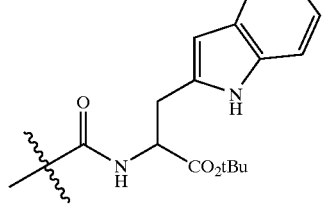 | G | 1.93 | 98 | 829 |
| 74 | CH | cHexyl | 3-(OH)Ph | CONHCH₂CO₂H | G | 1.59 | 100 | 644 |
| 75 | CH | cHexyl | 3-Cl-4-FPh | 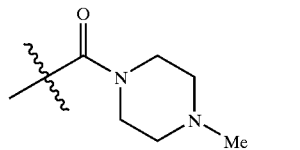 | G | 1.70 | 100 | 704 |
| 76 | CH | cHexyl | 3-Cl-4-FPh | 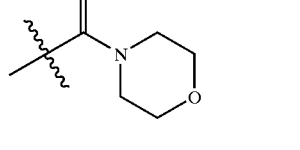 | G | 1.86 | 100 | 692 |
| 77 | CH | cHexyl | 3-Cl-4-FPh | 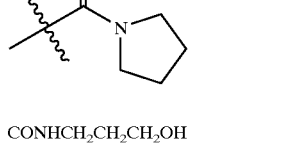 | G | 1.84 | 86 | 676 |
| 78 | CH | cHexyl | 3-Cl-4-FPh | CONHCH₂CH₂CH₂OH | G | 1.74 | 91 | 680 |
| 79 | CH | cHexyl | 3-Cl-4-FPh | CONHMe | G | 1.88 | 100 | 636 |
| 80 | CH | cHexyl | 3-Cl-4-FPh | 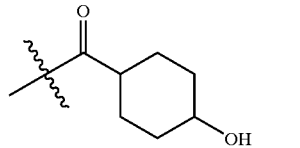 | G | 1.75 | 94 | 706 |
| 81 | CH | cHexyl | 3-Cl-4-FPh | CON(CH₂CH₂OH)₂ | G | 1.79 | 100 | 710 |
| 82 | CH | cHexyl | 3-Cl-4-FPh | CONHCH(Me)CO₂tBu | G | 1.91 | 90 | 750 |

-continued

Master Table.

[Structure: tetrazole-substituted benzimidazole core with R³ on N, connected to phenyl-O-CH2-phenyl bearing R⁴ (ortho) and R⁶ (para on second ring); Q position shown]

| Ex. No. | Q | R³ | R⁴ | R⁶ | Synthetic method | Retention Time (min) | Purity (AP) | MS (M + 1) |
|---|---|---|---|---|---|---|---|---|
| 83 | CH | cHexyl | 3-Cl-4-FPh | [structure: -C(Me)2-C(O)-NH-CH(CH2-C6H4-OH)-C(O)-OtBu] | G | 1.92 | 90 | 842 |
| 84 | CH | cHexyl | 3-Cl-4-FPh | CONHCH2CO2tBu | G | 1.98 | 98 | 736 |
| 85 | CH | cHexyl | 3-Cl-4-FPh | [structure: -C(Me)2-C(O)-NH-CH(CH2-indol-2-yl)-CO2tBu] | G | 2.00 | 85 | 865 |
| 86 | CH | cHexyl | 3-Cl-4-FPh | CONHCH2CO2H | G | 1.83 | 100 | 680 |
| 87 | CH | cHexyl | 3,4-di-MeOPh | [structure: -C(Me)2-C(O)-N-methylpiperazine] | G | 1.39 | 100 | 712 |
| 88 | CH | cHexyl | 3,4-di-MeOPh | [structure: -C(Me)2-C(O)-morpholine] | G | 1.67 | 95 | 700 |
| 89 | CH | cHexyl | 3,4-di-MeOPh | [structure: -C(Me)2-C(O)-pyrrolidine] | G | 1.76 | 100 | 684 |
| 90 | CH | cHexyl | 3,4-di-MeOPh | CONHCH2CH2CH2OH | G | 1.53 | 84 | 688 |
| 91 | CH | cHexyl | 3,4-di-MeOPh | CONHMe | G | 1.57 | 96 | 644 |

-continued

Master Table.

| Ex. No. | Q | R³ | R⁴ | R⁶ | Synthetic method | Retention Time (min) | Purity (AP) | MS (M + 1) |
|---|---|---|---|---|---|---|---|---|
| 92 | CH | cHexyl | 3,4-di-MeOPh |  | G | 1.54 | 95 | 713 |
| 93 | CH | cHexyl | 3,4-di-MeOPh | CON(CH₂CH₂OH)₂ | G | 1.56 | 100 | 718 |
| 94 | CH | cHexyl | 3,4-di-MeOPh | CONHCH(Me)CO₂tBu | G | 1.78 | 85 | 758 |
| 95 | CH | cHexyl | 3,4-di-MeOPh |  | G | 1.79 | 89 | 850 |
| 96 | CH | cHexyl | 3,4-di-MeOPh | CONHCH₂CO₂tBu | G | 1.71 | 93 | 744 |
| 97 | CH | cHexyl | 3,4-di-MeOPh |  | G | 1.88 | 95 | 873 |
| 98 | CH | cHexyl | 3,4-di-MeOPh | CONHCH₂CO₂H | G | 1.62 | 100 | 688 |
| 99 | CH | cHexyl | 4-ClPh |  | G | 1.74 | 95 | 688 |
| 100 | CH | cHexyl | 4-MeSPh | CONH₂ | G | 1.06 | 90 | 616 |
| 101 | CH | cHexyl | 4-MeSPh | CONHCH₂CH₂CONH₂ | G | 1.05 | 93 | 681 |
| 102 | CH | cHexyl | 4-MeSPh |  | G | 1.05 | 95 | 700 |
| 103 | CH | cHexyl | 4-MeSPh | CONHCH₂CO₂tBu | G | 1.10 | 90 | 730 |
| 104 | CH | cHexyl | 4-MeSPh | CONMe₂ | G | 1.07 | 96 | 644 |
| 105 | CH | cHexyl | 4-CNPh | CONHMe₂ | G | 1.59 | 85 | 623 |

Master Table.

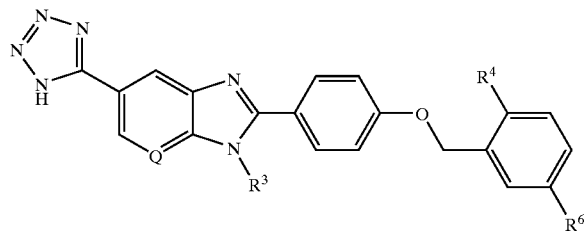

| Ex. No. | Q | R³ | R⁴ | R⁶ | Synthetic method | Retention Time (min) | Purity (AP) | MS (M + 1) |
|---|---|---|---|---|---|---|---|---|
| 106 | CH | cHexyl | 4-ClPh | CONHMe | G | 1.73 | 90 | 618 |
| 107 | CH | cHexyl | 4-ClPh | *(4-hydroxypiperidinyl carbonyl)* | G | 1.71 | 90 | 688 |
| 108 | CH | cHexyl | 4-ClPh | CONHCH₂CO₂tBu | G | 1.85 | 75 | 718 |
| 109 | CH | cHexyl | 4-ClPh | CONHCH₂CO₂H | G | 1.71 | 90 | 662 |
| 110 | CH | cHexyl | 4-ClPh | CONH₂ | G | 1.71 | 90 | 604 |
| 111 | CH | cHexyl | 4-ClPh | CONHCH₂CH₂NH₂ | G | 1.68 | 85 | 675 |
| 112 | CH | cHexyl | 4-ClPh | CONMe₂ | G | 1.75 | 85 | 632 |
| 113 | CH | cHexyl | 4-MeSPh | CONHMe | G | 1.06 | 90 | 630 |
| 114 | CH | cHexyl | 2-thienyl | CO₂H | D | 1.78 | 95 | 577 |
| 115 | CH | cHexyl | 3-thienyl | CO₂H | D | 1.77 | 95 | 577 |
| 116 | CH | cHexyl | 2-benzofuranyl | CO₂H | D | 1.91 | 90 | 611 |
| 117 | CH | cHexyl | 2-furanyl | CO₂H | D | 1.86 | 85 | 561 |
| 118 | CH | cHexyl | 3,4-dioxolanePh | CO₂H | D | 1.77 | 98 | 615 |
| 119 | CH | cHexyl | 2-benzothiophenyl | CO₂H | D | 2.07 | 95 | 627 |
| 120 | CH | cHexyl | 5-Ac-2-thienyl | CO₂H | D | 1.91 | 98 | 619 |
| 121 | CH | cHexyl | 5-indolyl | CO₂H | D | 1.90 | 97 | 610 |
| 122 | CH | cHexyl | 3-CHO-2-furanyl | CO₂H | D | 1.65 | 85 | 589 |
| 123 | CH | cHexyl | 8-quinolinyl | CO₂H | D | 1.67 | 90 | 622 |
| 124 | CH | cHexyl | 2-indolyl | CO₂H | D | 1.75 | 95 | 609 |
| 125 | CH | cHexyl | 2,4-di-MeO-5-pyrimidinyl | CO₂H | D | 1.91 | 95 | 632 |
| 126 | CH | cHexyl | N-BOC-2-pyrrolyl | CO₂H | D | 1.81 | 92 | 659 |
| 127 | CH | cHexyl | N-Me-5-indolyl | CO₂H | D | 1.80 | 98 | 623 |
| 128 | CH | cHexyl | 5-pyrimidinyl | CO₂H | D | 1.60 | 98 | 572 |
| 129 | CH | cHexyl | 3-thienyl | *(tyrosine amide)* | G | 1.54 | 92 | 740 |
| 130 | CH | cHexyl | 3-thienyl | *(tryptophan amide)* | G | 1.91 | 100 | 763 |

Master Table.
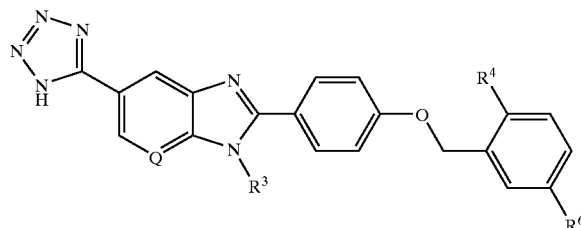
| Ex. No. | Q | R³ | R⁴ | R⁶ | Synthetic method | Retention Time (min) | Purity (AP) | MS (M + 1) |
|---|---|---|---|---|---|---|---|---|
| 131 | CH | cHexyl | 3-thienyl | CONHCH₂CH₂CONH₂ | G | 1.60 | 98 | 647 |
| 132 | CH | cHexyl | 3-thienyl | 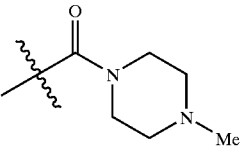 | G | 1.56 | 100 | 659 |
| 133 | CH | cHexyl | 3-thienyl | 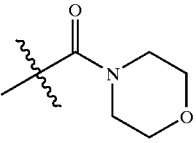 | G | 1.74 | 100 | 646 |
| 134 | CH | cHexyl | 3-thienyl | 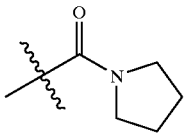 | G | 1.72 | 100 | 630 |
| 135 | CH | cHexyl | 3-thienyl | CONHCH₂CH₂CH₂OH | G | 1.71 | 92 | 634 |
| 136 | CH | cHexyl | 3-thienyl | CONHMe | G | 1.73 | 100 | 590 |
| 137 | CH | cHexyl | 3-thienyl | 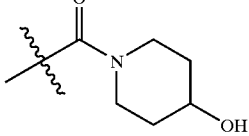 | G | 1.71 | 95 | 660 |
| 138 | CH | cHexyl | 3-thienyl | CON(CH₂CH₂OH)₂ | G | 1.63 | 100 | 664 |
| 139 | CH | cHexyl | 3-thienyl | CONH(Me)CO₂tBu | G | 1.80 | 77 | 704 |
| 140 | CH | cHexyl | 3-thienyl | 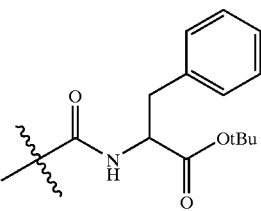 | G | 1.91 | 92 | 796 |

-continued

Master Table.

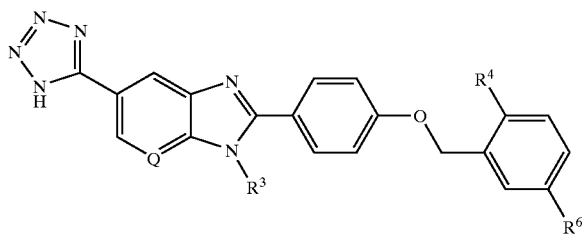

| Ex. No. | Q | R³ | R⁴ | R⁶ | Synthetic method | Retention Time (min) | Purity (AP) | MS (M + 1) |
|---|---|---|---|---|---|---|---|---|
| 141 | CH | cHexyl | 3-thienyl | CONHCH$_2$CO$_2$tBu | G | 1.86 | 94 | 690 |
| 142 | CH | cHexyl | 3-thienyl | | G | 1.90 | 95 | 819 |
| 143 | CH | cHexyl | 3-thienyl | CONHCH$_2$CO$_2$H | G | 1.58 | 98 | 634 |
| 144 | CH | cHexyl | 5-Ac-2-thienyl | CONHCH$_2$CO$_2$tBu | G | 1.55 | 95 | 731 |
| 145 | CH | cHexyl | 5-Ac-2-thienyl | CONHCH$_2$CO$_2$H | G | 1.48 | 90 | 676 |
| 146 | CH | cHexyl | 5-Ac-2-thienyl | CONH$_2$ | G | 1.58 | 94 | 618 |
| 147 | CH | cHexyl | 5-Ac-2-thienyl | CONHCH$_2$CH$_2$CONH$_2$ | G | 1.44 | 91 | 689 |
| 148 | CH | cHexyl | 5-Ac-2-thienyl | CONMe$_2$ | G | 1.37 | 85 | 646 |
| 149 | CH | cHexyl | 4-(CN)Ph | | G | 1.36 | 95 | 679 |
| 150 | CH | cHexyl | 5-Ac-2-thienyl | CONHMe | G | 1.51 | 92 | 632 |
| 151 | CH | cHexyl | 5-Ac-2-thienyl | | G | 1.47 | 90 | 702 |
| 152 | CH | cHexyl | 3-CF$_3$CO-5-indolyl | CONHMe$_2$ | G | 1.58 | 100 | 733 |
| 153 | CH | cHexyl | 3-CF$_3$CO-5-indolyl | CONHCH$_2$CO$_2$H | G | 1.55 | 83 | 763 |
| 154 | CH | cHexyl | 3-CF$_3$CO-5-indolyl | CONH$_2$ | G | 1.69 | 86 | 706 |
| 155 | CH | cHexyl | 3-CF$_3$CO-5-indolyl | CONHCH$_2$CH$_2$CONH$_2$ | G | 1.52 | 80 | 776 |

UTILITY

The compounds of Formula I inhibit the activity of Hepatitis C Virus NS5B RdRp as demonstrated using assays for NS5B RdRp activity. Thus, the compounds of Formula I are potentially useful in the cure and prevention of HCV infections.

HCV NS5B RdRp cloning, expression and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 ug/ml and the cells were grown overnight at 20° C.

Cell pellets (3L) were lysed for purification to yield 15–24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 $\mu$m filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5–50 column volumes depending on the column type. After the final chromatography step, the resulting purity of the enzyme is >90% based on SDS-PAGE analysis. The enzyme was aliquoted and stored at −80° C.

HCV NS5B RdRp enzyme assay. HCV RdRp genotype 1b assays were run in assay buffer composed of 20 mM Tris-HCl, pH 7.5, 2.5 mM KCl, 5 mM $MgCl_2$, 1 mM DTT, 1.6 U RNAse inhibitor (Promega N2515), in 96 well plates (Falcon 3918). All compounds were serially diluted in DMSO and diluted further in assay buffer such that the final concentration of DMSO in the assay was 2%. Compounds were serially diluted (3-fold each time) for a 7 point inhibition analysis. HCV RdRp genotype 1b enzyme was used at a final concentration of 28 nM. A polyA template was used at 28 nM, and the oligo-$dT_{12-18}$ primer was used at 840 nM final concentration. Preannealed primer and template were obtained commercially (Amersham 27-787802). $^3$H-UTP was used at 0.125 $\mu$Ci (1 $\mu$M total UTP). Reaction was initiated by the addition of enzyme. Reactions were incubated at 30° C. for 45 min, and stopped by adding 30 ul of 20% ice cold TCA. Plates were chilled for 30 minutes and harvested onto Unifilter-96, GF/B plates (Packard, 6005177) using a Packard FilterMate Cell Harvester. The harvest plates were prewashed 3 times, 200 ul/well, with 100 mM NaPPi. Harvested filters were washed 30 times, 200 ul/well, with distilled water followed by ethanol. Filter plates were dried, and 30 ul/well microscint-20 was added. Plates were read on a Packard Top Count NXT.

The $IC_{50}$ values for compounds were determined using six different [I], combined with 7 nM enzyme, 800 ng of the template-primer polyC/oligo$G_{12}$ (1:5 molar ratio), and 0.7 uM of $^3$H GTP containing 1 uCi. The observed fractional activity (fa=vi/vo) was used in the equation $IC_{50}$=[I]/(1/fa-1) to determine a single point $IC_{50}$ value. Typically, the single point $IC_{50}$ values derived from [I] that produced fractional activities in the range of 0.1 to 0.8 relative to the uninhibited control were averaged to calculate the $IC_{50}$ value for each compound.

The HCV NS5B RdRp enzyme assay results are tabulated in the following table.

| Example No. | IC50 ($\mu$M) |
|---|---|
| 1 | 0.63 |
| 3 | 0.14 |
| 4 | 0.63 |
| 5 | 0.36 |
| 10 | 0.85 |
| 17 | 5.21 |
| 18 | 1.52 |
| 20 | 8.20 |
| 22 | 8.09 |
| 23 | 0.02 |
| 24 | 0.05 |
| 25 | 0.04 |
| 26 | 0.19 |
| 27 | 1.01 |
| 28 | 0.62 |
| 29 | 0.25 |
| 30 | 0.04 |
| 31 | 0.06 |
| 32 | 0.04 |
| 33 | 0.04 |
| 34 | 0.04 |
| 35 | 0.07 |
| 36 | 0.83 |
| 37 | 0.07 |
| 38 | 0.00 |
| 39 | 0.01 |
| 40 | 0.08 |
| 41 | 0.05 |
| 42 | 0.05 |
| 43 | 0.24 |
| 44 | 0.08 |
| 45 | 0.08 |
| 46 | 0.06 |
| 47 | 0.05 |
| 48 | 0.32 |
| 49 | 0.08 |
| 50 | 0.23 |
| 51 | 0.93 |
| 52 | 0.47 |
| 53 | 0.57 |
| 54 | 0.68 |
| 55 | 0.20 |
| 56 | 0.19 |
| 57 | 0.18 |
| 58 | 0.38 |
| 59 | 0.92 |
| 60 | 0.28 |
| 61 | 0.09 |
| 62 | 0.11 |
| 63 | 0.15 |
| 64 | 1.20 |
| 65 | 1.70 |
| 66 | 1.40 |
| 67 | 0.79 |
| 68 | 0.54 |
| 69 | 0.66 |
| 70 | 0.50 |
| 71 | 0.52 |
| 72 | 0.93 |
| 73 | 1.30 |
| 74 | 0.15 |
| 75 | 0.35 |
| 76 | 1.40 |
| 77 | 1.20 |
| 78 | 0.69 |
| 79 | 0.55 |
| 80 | 0.94 |
| 81 | 1.10 |
| 82 | 1.30 |
| 83 | 0.56 |
| 84 | 1.20 |
| 85 | 2.30 |
| 86 | 0.32 |
| 87 | 0.43 |
| 88 | 0.47 |
| 89 | 0.46 |

| Example No. | IC50 (μM) |
|---|---|
| 90 | 0.63 |
| 91 | 0.26 |
| 92 | 0.30 |
| 93 | 0.69 |
| 94 | 2.10 |
| 95 | 1.40 |
| 96 | 1.60 |
| 97 | 2.20 |
| 98 | 0.21 |
| 99 | 0.86 |
| 106 | 0.66 |
| 114 | 0.07 |
| 115 | 0.04 |
| 116 | 0.17 |
| 117 | 0.29 |
| 118 | 0.07 |
| 119 | 0.03 |
| 120 | 0.02 |
| 121 | 0.03 |
| 122 | 0.67 |
| 123 | 0.44 |
| 124 | 0.12 |
| 125 | 1.28 |
| 126 | 0.46 |
| 127 | 0.09 |
| 128 | 1.04 |
| 129 | 0.29 |
| 130 | 0.58 |
| 131 | 0.23 |
| 132 | 0.83 |
| 133 | 1.10 |
| 134 | 0.37 |
| 135 | 0.70 |
| 136 | 0.22 |
| 137 | 1.30 |
| 138 | 3.00 |
| 139 | 2.60 |
| 140 | 2.15 |
| 141 | 2.80 |
| 142 | 1.20 |
| 143 | 0.08 |
| 149 | 0.22 |
| 152 | 0.42 |
| 153 | 0.26 |
| 154 | 0.33 |
| 155 | 0.27 |
We claim:
1. A compound of Formula I
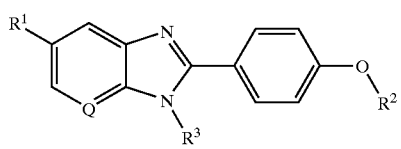
wherein:
Q is N;
$R^1$ is tetrazolyl, MeCONHSO$_2$—, PhCONHSO$_2$—, $R^5O_2C(CH_2)_{0-3}CONHSO_2$—,
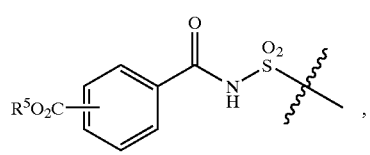
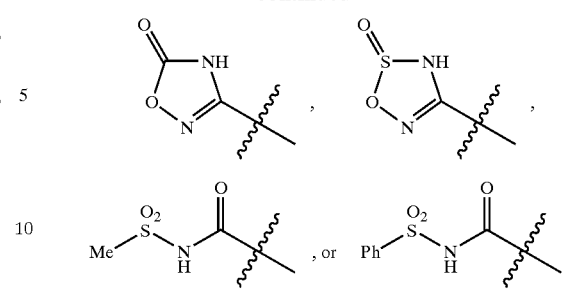
$R^2$ is
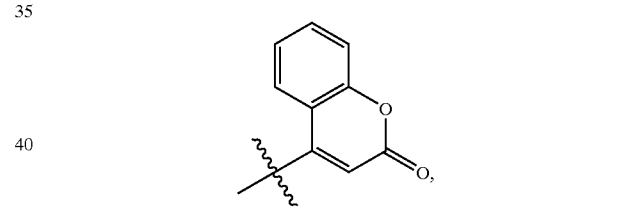
—CH$_2$Ar$^1$, —CHPh$_2$, —CH$_2$CO(4-FPh), —CH$_2$CO(4-CF$_3$Ph), or —CH$_2$CONp where Np is naphthyl;
$R^3$ is C$_{5-7}$cycloalkyl;
$R^4$ is hydrogen, Ar$^2$, or Ar$^3$;
Ar$^1$ is selected from the following group: phenyl, halophenyl,
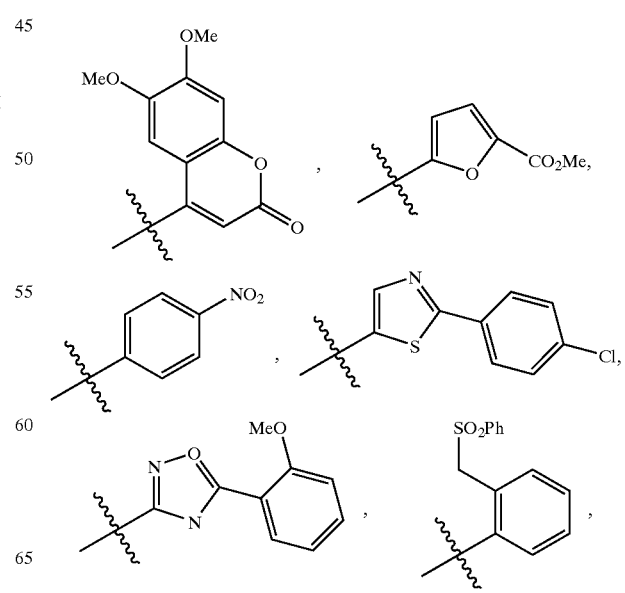

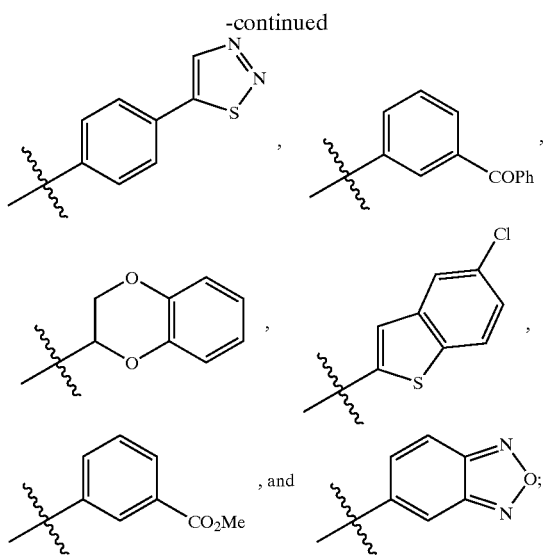

Ar² is phenyl, naphthyl, or biphenyl, optionally substituted with 1–3 substituents selected from the group comprising halogen, $C_{1-6}$ alkyl, hydroxy$C_{1-6}$alkyl, $C_{1-6}$alkoxy, $C_{1-6}$sulfoxy, $C_{1-2}$perfluoroalkyl, hydroxy, formyl, $C_{1-6}$alkylcarbonyl, cyano, nitro, $C_{1-6}$alkylamido, $CO_2R^5$, $CONR^5R^5$, $C_{1-6}$alkylsulfonamido, and dioxolane;

Ar³ is thienyl, furanyl, pyrrolyl, benzothiophenyl, benzofuranyl, indolyl, quinolinyl, or pyrimidinyl optionally substituted with 1–2 substituents selected from the group comprising $C_{1-6}$alkyl, formyl, acetoxy, trifluoroacetoxy, and t-butoxycarbonyl;

$R^5$ is hydrogen or $C_{1-6}$alkyl;

$R^6$ is halogen, methoxy, $CO_2R^5$ or $CONR^7R^8$;

$R^7$ and $R^8$ are independently hydrogen, $C_{1-6}$alkyl, —CH(Me)$CO_2R^5$, —$(CH_2)_{1-3}CO_2R^5$, —$(CH_2)_{1-3}CONR^5R^5$, —$(CH_2)_{1-3}OH$,

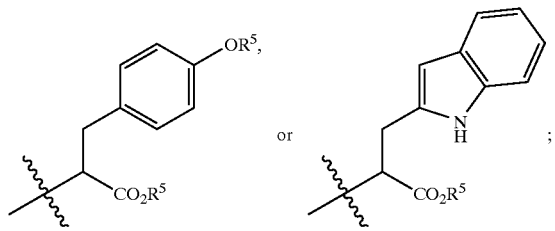

or $R^7$ and $R^8$ taken together with the nitrogen to which they are attached form pyrrolidine, morpholine, piperidine, 4-hydroxypiperidine, piperazine, or 4-methylpiperazine;

or a pharmaceutically acceptable salt, solvate, or prodrug thereof.

2. A compound of claim 1 wherein $R^3$ is cyclohexyl.

3. A compound of claim 1 wherein $R^1$ is tetrazolyl and $R^2$ is

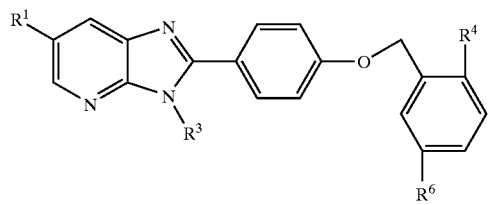

4. A compound of claim 3 wherein $R^4$ is Ar².

5. A compound of claim 4 wherein $R^3$ is cyclohexyl.

6. A compound of claim 3 wherein $R^4$ is Ar³.

7. A compound of claim 6 wherein $R^3$ is cyclohexyl.

8. A compound of claim 3 wherein $R^4$ hydrogen.

9. A compound of claim 8 wherein $R^3$ is cyclohexyl.

10. A compound of claim 1 wherein $R^2$ is —$CH_2Ar^1$.

11. A compound of claim 10 wherein $R^3$ is cyclohexyl.

12. A composition useful for treating hepatitus C comprising a therapeutic amount of a compound of claim 1 and a pharmaceutically acceptable carrier.

13. A method for treating hepatitus C comprising administering a therapeutically effective amount of a compound of claim 1 to a patient in need thereof.

14. A compound of Formula Ia

Ia

[Formula Ia structure]

wherein:

$R^1$ is tetrazolyl or MeCONHSO$_2$—;

$R^3$ is $C_{5-7}$cycloalkyl;

$R^4$ is phenyl substituted with halogen or cyano;

$R^6$ is methoxy or $CONR^7R^8$;

$R^7$ and $R^8$ are independently hydrogen or $C_{1-6}$alkyl;

or a pharmaceutically acceptable salt, solvate, or prodrug thereof.

15. A compound of claim 14 selected from the group consisting of;

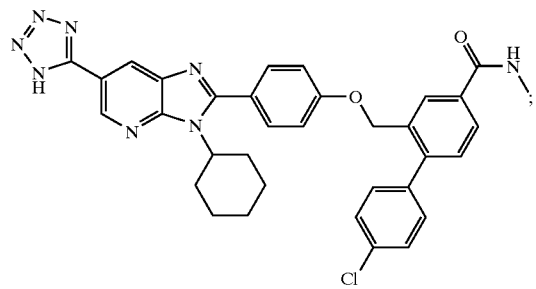

79
-continued
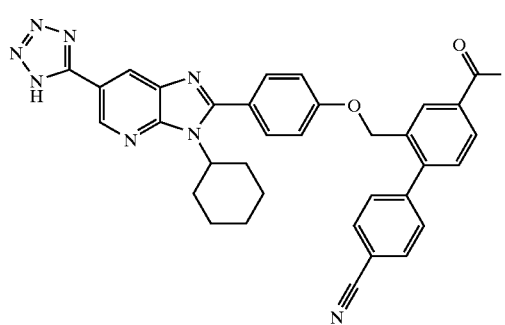
; and
80
-continued
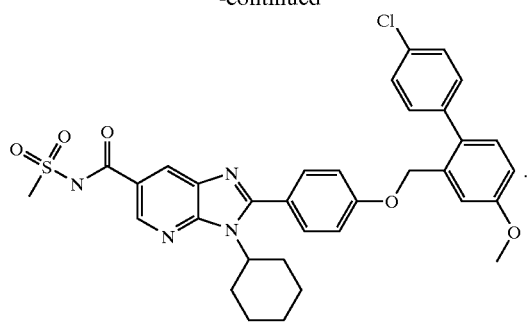
.
* * * * *